United States Patent
Ben-Haim et al.

(10) Patent No.: US 9,275,451 B2
(45) Date of Patent: Mar. 1, 2016

(54) METHOD, A SYSTEM, AND AN APPARATUS FOR USING AND PROCESSING MULTIDIMENSIONAL DATA

(75) Inventors: Shlomo Ben-Haim, London (GB); Benny Rousso, Rishon-LeZion (IL)

(73) Assignee: Biosensors International Group, Ltd., Hamilton (BM)

( * ) Notice: Subject to any disclaimer, the term of this patent is extended or adjusted under 35 U.S.C. 154(b) by 738 days.

(21) Appl. No.: 12/448,473

(22) PCT Filed: Dec. 20, 2007

(86) PCT No.: PCT/IL2007/001588
§ 371 (c)(1),
(2), (4) Date: Jan. 12, 2010

(87) PCT Pub. No.: WO2008/075362
PCT Pub. Date: Jun. 26, 2008

(65) Prior Publication Data
US 2010/0142774 A1    Jun. 10, 2010

Related U.S. Application Data

(60) Provisional application No. 60/875,833, filed on Dec. 20, 2006.

(51) Int. Cl.
*G06T 7/00* (2006.01)
*G06F 19/00* (2011.01)

(52) U.S. Cl.
CPC ............ *G06T 7/0012* (2013.01); *G06F 19/321* (2013.01); *G06F 19/324* (2013.01)

(58) Field of Classification Search
CPC ........... G06T 2207/10116; G06T 2207/10081; G06T 5/009; G06T 2207/30004; G06T 2207/10104; G06T 7/0012; G06T 2207/10072; A61B 5/055; A61B 5/1127; A61B 6/037; A61B 6/481; G06F 19/321; G06F 17/30265; A61N 5/1049; A61N 5/103; A61N 5/1031; G06K 9/00664; G06K 9/00711
USPC .................................. 382/128, 134, 224, 228
See application file for complete search history.

(56) References Cited

U.S. PATENT DOCUMENTS

| 630,611 A | 8/1899 | Knapp et al. |
| 2,776,377 A | 1/1957 | Anger |

(Continued)

FOREIGN PATENT DOCUMENTS

| DE | 1516429 | 12/1969 |
| DE | 19814199 | 10/1999 |

(Continued)

OTHER PUBLICATIONS

Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.

(Continued)

*Primary Examiner* — Edward Park

(57) ABSTRACT

A method for analyzing a functional map of at least one tissue of a patient. The method comprises managing a plurality of functional maps each being associated with a plurality of first biological activity indications, receiving a functional map which is associated with a plurality of second biological activity indications, identifying a matching set of the managed functional maps by matching between the plurality of first and second biological activity indications, and using the matching set for a member of a group consisting of: an image data acquisition, a diagnosis of the received functional map, a classification of the received functional map.

45 Claims, 4 Drawing Sheets

(56) References Cited

U.S. PATENT DOCUMENTS

| | | | |
|---|---|---|---|
| 3,340,866 A | 9/1967 | Nöller | |
| 3,446,965 A | 5/1969 | Ogier et al. | |
| 3,535,085 A | 10/1970 | Shumate et al. | |
| 3,684,887 A | 8/1972 | Hugonin | |
| 3,690,309 A | 9/1972 | Pluzhnikov et al. | |
| 3,719,183 A | 3/1973 | Schwartz | |
| 3,739,279 A | 6/1973 | Hollis | |
| 3,971,362 A | 7/1976 | Pope et al. | |
| 3,978,337 A | 8/1976 | Nickles et al. | |
| 3,988,585 A | 10/1976 | O'Neill et al. | |
| 4,000,502 A | 12/1976 | Butler et al. | |
| 4,015,592 A | 4/1977 | Bradley-Moore | |
| 4,055,765 A | 10/1977 | Gerber et al. | |
| 4,061,919 A | 12/1977 | Miller et al. | |
| 4,095,107 A | 6/1978 | Genna et al. | |
| 4,165,462 A | 8/1979 | Macovski et al. | |
| 4,181,856 A | 1/1980 | Bone | |
| 4,278,077 A | 7/1981 | Mizumoto | |
| 4,289,969 A | 9/1981 | Cooperstein et al. | |
| 4,291,708 A | 9/1981 | Frei et al. | |
| 4,296,785 A | 10/1981 | Vitello et al. | |
| 4,302,675 A | 11/1981 | Wake et al. | |
| 4,364,377 A | 12/1982 | Smith | |
| 4,383,327 A | 5/1983 | Kruger | |
| 4,476,381 A | 10/1984 | Rubin | |
| 4,503,331 A | 3/1985 | Kovacs, Jr. et al. | |
| 4,521,688 A | 6/1985 | Yin | |
| H12 H | 1/1986 | Bennett et al. | |
| 4,580,054 A | 4/1986 | Shimoni | |
| 4,595,014 A | 6/1986 | Barrett et al. | |
| 4,674,107 A | 6/1987 | Urban et al. | |
| 4,679,142 A | 7/1987 | Lee | |
| 4,689,041 A | 8/1987 | Corday et al. | |
| 4,689,621 A | 8/1987 | Kleinberg | |
| 4,709,382 A | 11/1987 | Sones | |
| 4,710,624 A | 12/1987 | Alvarez et al. | |
| 4,731,536 A | 3/1988 | Rische et al. | |
| 4,773,430 A | 9/1988 | Porath | |
| 4,782,840 A | 11/1988 | Martin, Jr. et al. | |
| 4,791,934 A | 12/1988 | Brunnett | |
| 4,801,803 A | 1/1989 | Denen et al. | |
| 4,828,841 A | 5/1989 | Porter et al. | |
| 4,834,112 A | 5/1989 | Machek et al. | |
| 4,844,067 A | 7/1989 | Ikada et al. | |
| 4,844,076 A | 7/1989 | Lesho et al. | |
| 4,853,546 A | 8/1989 | Abe et al. | |
| 4,854,324 A | 8/1989 | Hirschman et al. | |
| 4,854,330 A | 8/1989 | Evans, III et al. | |
| 4,867,962 A | 9/1989 | Abrams | |
| 4,893,013 A | 1/1990 | Denen et al. | |
| 4,893,322 A | 1/1990 | Hellmick et al. | |
| 4,919,146 A | 4/1990 | Rhinehart et al. | |
| 4,924,486 A | 5/1990 | Weber et al. | |
| 4,928,250 A | 5/1990 | Greenberg et al. | |
| 4,929,832 A | 5/1990 | Ledly | |
| 4,938,230 A | 7/1990 | Machek et al. | |
| 4,951,653 A | 8/1990 | Fry et al. | |
| 4,959,547 A | 9/1990 | Carroll et al. | |
| 4,970,391 A | 11/1990 | Uber, III | |
| 4,995,396 A | 2/1991 | Inaba et al. | |
| 5,014,708 A | 5/1991 | Hayashi et al. | |
| 5,018,182 A | 5/1991 | Cowan et al. | |
| 5,032,729 A | 7/1991 | Charpak | |
| 5,033,998 A | 7/1991 | Corday et al. | |
| 5,039,863 A | 8/1991 | Matsuno et al. | |
| 5,042,056 A | 8/1991 | Hellmick et al. | |
| 5,070,877 A | 12/1991 | Mohiuddin et al. | |
| 5,070,878 A | 12/1991 | Denen | |
| 5,088,492 A | 2/1992 | Takayama et al. | |
| 5,115,137 A | 5/1992 | Andersson-Engels et al. | |
| 5,119,818 A | 6/1992 | Carroll et al. | |
| 5,132,542 A | 7/1992 | Bassalleck et al. | |
| 5,142,557 A | 8/1992 | Toker et al. | |
| 5,145,163 A | 9/1992 | Cowan et al. | |
| 5,151,598 A | 9/1992 | Denen | |
| 5,170,055 A | 12/1992 | Carroll et al. | |
| 5,170,439 A | 12/1992 | Zeng et al. | |
| 5,170,789 A | 12/1992 | Narayan et al. | |
| 5,196,796 A | 3/1993 | Misic et al. | |
| 5,210,421 A | 5/1993 | Gullberg et al. | |
| 5,243,988 A | 9/1993 | Sieben et al. | |
| 5,246,005 A | 9/1993 | Carroll et al. | |
| 5,249,124 A | 9/1993 | DeVito | |
| 5,252,830 A | 10/1993 | Weinberg | |
| 5,254,101 A | 10/1993 | Trombley, III | |
| 5,258,717 A | 11/1993 | Misic et al. | |
| 5,263,077 A | 11/1993 | Cowan et al. | |
| 5,279,607 A | 1/1994 | Schentag et al. | |
| 5,284,147 A | 2/1994 | Hanaoka et al. | |
| 5,299,253 A | 3/1994 | Wessels | |
| 5,304,165 A | 4/1994 | Haber et al. | |
| 5,307,808 A | 5/1994 | Dumoulin et al. | |
| 5,307,814 A | 5/1994 | Kressel et al. | |
| 5,309,959 A | 5/1994 | Shaw et al. | |
| 5,317,506 A | 5/1994 | Coutre et al. | |
| 5,317,619 A | 5/1994 | Hellmick et al. | |
| 5,323,006 A | 6/1994 | Thompson et al. | |
| 5,329,976 A | 7/1994 | Haber et al. | |
| 5,334,141 A | 8/1994 | Carr et al. | |
| 5,349,190 A | 9/1994 | Hines et al. | |
| 5,355,087 A | 10/1994 | Claiborne et al. | |
| 5,365,069 A | 11/1994 | Eisen et al. | |
| 5,365,928 A | 11/1994 | Rhinehart et al. | |
| 5,367,552 A | 11/1994 | Peschmann | |
| 5,377,681 A | 1/1995 | Drane | |
| 5,381,791 A * | 1/1995 | Qian ............................ 600/436 |
| 5,383,456 A | 1/1995 | Arnold et al. | |
| 5,383,858 A | 1/1995 | Reilly et al. | |
| 5,386,446 A | 1/1995 | Fujimoto et al. | |
| 5,387,409 A | 2/1995 | Nunn et al. | |
| 5,391,877 A | 2/1995 | Marks | |
| 5,395,366 A | 3/1995 | D'Andrea | |
| 5,396,531 A | 3/1995 | Hartley | |
| 5,399,868 A | 3/1995 | Jones et al. | |
| 5,404,293 A | 4/1995 | Weng et al. | |
| 5,415,181 A | 5/1995 | Hofgrefe et al. | |
| 5,431,161 A | 7/1995 | Ryals et al. | |
| 5,435,302 A | 7/1995 | Lenkinski et al. | |
| 5,436,458 A | 7/1995 | Tran et al. | |
| 5,441,050 A | 8/1995 | Thurston et al. | |
| 5,448,073 A | 9/1995 | Jeanguillaume | |
| 5,451,232 A | 9/1995 | Rhinehart et al. | |
| 5,472,403 A | 12/1995 | Cornacchia et al. | |
| 5,475,219 A | 12/1995 | Olson | |
| 5,475,232 A | 12/1995 | Powers et al. | |
| 5,476,095 A | 12/1995 | Schnall et al. | |
| 5,479,969 A | 1/1996 | Hardie et al. | |
| 5,481,115 A | 1/1996 | Hsieh et al. | |
| 5,484,384 A | 1/1996 | Fearnot | |
| 5,489,782 A | 2/1996 | Wernikoff | |
| 5,493,595 A | 2/1996 | Schoolman | |
| 5,493,805 A | 2/1996 | Penuela et al. | |
| 5,494,036 A | 2/1996 | Uber, III et al. | |
| 5,501,674 A | 3/1996 | Trombley, III et al. | |
| 5,517,120 A | 5/1996 | Misik et al. | |
| 5,519,221 A | 5/1996 | Weinberg | |
| 5,519,222 A | 5/1996 | Besett | |
| 5,519,931 A | 5/1996 | Reich | |
| 5,520,182 A | 5/1996 | Leighton et al. | |
| 5,520,653 A | 5/1996 | Reilly et al. | |
| 5,521,506 A | 5/1996 | Misic et al. | |
| 5,536,945 A | 7/1996 | Reich | |
| 5,545,899 A | 8/1996 | Tran et al. | |
| 5,559,335 A | 9/1996 | Zeng et al. | |
| 5,565,684 A | 10/1996 | Gullberg et al. | |
| 5,569,181 A | 10/1996 | Heilman et al. | |
| 5,572,132 A | 11/1996 | Pulyer et al. | |
| 5,572,999 A | 11/1996 | Funda et al. | |
| 5,579,766 A | 12/1996 | Gray | |
| 5,580,541 A | 12/1996 | Wells et al. | |
| 5,585,637 A | 12/1996 | Bertelsen et al. | |
| 5,587,585 A | 12/1996 | Eisen et al. | |
| 5,591,143 A | 1/1997 | Trombley, III et al. | |
| 5,600,145 A | 2/1997 | Plummer | |

(56) References Cited

U.S. PATENT DOCUMENTS

| | | | |
|---|---|---|---|
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |
| 5,630,034 A | 5/1997 | Oikawa et al. |
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,250 A | 11/1997 | Curley et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,799,111 A | 8/1998 | Guissin |
| 5,800,355 A * | 9/1998 | Hasegawa ............... 600/436 |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,818,050 A | 10/1998 | Dilmanian et al. |
| 5,821,541 A | 10/1998 | Tümer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A | 6/1999 | Judd et al. |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber, III et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |

(56) References Cited

U.S. PATENT DOCUMENTS

| | | |
|---|---|---|
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,244 B1 | 5/2002 | Gagnon |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 | 6/2002 | Cardin et al. |
| 6,415,046 B1 | 7/2002 | Kerut, Sr. |
| 6,420,711 B2 | 7/2002 | Tuemer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 * | 5/2003 | Takeo et al. .................. 382/132 |
| 6,565,502 B1 | 5/2003 | Bede et al. |
| 6,567,687 B2 | 5/2003 | Front et al. |
| 6,574,304 B1 | 6/2003 | Hsieh et al. |
| 6,575,930 B1 | 6/2003 | Trombley, III et al. |
| 6,576,918 B1 | 6/2003 | Fu et al. |
| 6,583,420 B1 | 6/2003 | Nelson et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |

(56) References Cited

U.S. PATENT DOCUMENTS

| | | |
|---|---|---|
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |
| 6,798,206 B2 | 9/2004 | Misic |
| 6,808,513 B2 | 10/2004 | Reilly et al. |
| 6,809,321 B2 | 10/2004 | Rempel |
| 6,813,868 B2 | 11/2004 | Baldwin et al. |
| 6,821,013 B2 | 11/2004 | Reilly et al. |
| 6,822,237 B2 | 11/2004 | Inoue et al. |
| 6,833,705 B2 | 12/2004 | Misic |
| 6,838,672 B2 | 1/2005 | Wagenaar et al. |
| 6,841,782 B1 | 1/2005 | Balan et al. |
| 6,843,357 B2 | 1/2005 | Bybee et al. |
| 6,851,615 B2 | 2/2005 | Jones |
| 6,866,654 B2 | 3/2005 | Callan et al. |
| 6,870,175 B2 | 3/2005 | Dell et al. |
| 6,881,043 B2 | 4/2005 | Barak |
| 6,888,351 B2 | 5/2005 | Belt et al. |
| 6,889,074 B2 | 5/2005 | Uber, III et al. |
| 6,897,658 B2 | 5/2005 | Belt et al. |
| 6,906,330 B2 | 6/2005 | Blevis et al. |
| D507,832 S | 7/2005 | Yanniello et al. |
| 6,915,170 B2 | 7/2005 | Engleson et al. |
| 6,915,823 B2 | 7/2005 | Osborne et al. |
| 6,917,828 B2 | 7/2005 | Fukuda |
| 6,921,384 B2 | 7/2005 | Reilly et al. |
| 6,928,142 B2 | 8/2005 | Shao et al. |
| 6,935,560 B2 | 8/2005 | Andreasson et al. |
| 6,936,030 B1 | 8/2005 | Pavlik et al. |
| 6,937,750 B2 | 8/2005 | Natanzon et al. |
| 6,939,302 B2 | 9/2005 | Griffiths et al. |
| 6,940,070 B2 | 9/2005 | Tumer |
| 6,943,355 B2 | 9/2005 | Shwartz et al. |
| 6,957,522 B2 | 10/2005 | Baldwin et al. |
| 6,958,053 B1 | 10/2005 | Reilly |
| 6,963,770 B2 | 11/2005 | Scarantino et al. |
| 6,970,735 B2 | 11/2005 | Uber, III et al. |
| 6,972,001 B2 | 12/2005 | Emig et al. |
| 6,974,443 B2 | 12/2005 | Reilly et al. |
| 6,976,349 B2 | 12/2005 | Baldwin et al. |
| 6,984,222 B1 | 1/2006 | Hitchins et al. |
| 6,985,870 B2 | 1/2006 | Martucci et al. |
| 6,988,981 B2 | 1/2006 | Hamazaki |
| 6,994,249 B2 | 2/2006 | Peterka et al. |
| 7,009,183 B2 | 3/2006 | Wainer et al. |
| 7,011,814 B2 | 3/2006 | Suddarth et al. |
| 7,012,430 B2 | 3/2006 | Misic |
| 7,017,622 B2 | 3/2006 | Osborne et al. |
| 7,018,363 B2 | 3/2006 | Cowan et al. |
| 7,019,783 B2 | 3/2006 | Kindem et al. |
| 7,025,757 B2 | 4/2006 | Reilly et al. |
| 7,026,623 B2 | 4/2006 | Oaknin et al. |
| 7,043,063 B1 | 5/2006 | Noble et al. |
| 7,102,138 B2 | 9/2006 | Belvis et al. |
| 7,103,204 B1 | 9/2006 | Celler et al. |
| 7,127,026 B2 | 10/2006 | Amemiya et al. |
| 7,142,634 B2 | 11/2006 | Engler et al. |
| 7,145,986 B2 | 12/2006 | Wear et al. |
| 7,147,372 B2 | 12/2006 | Nelson et al. |
| 7,164,130 B2 | 1/2007 | Welsh et al. |
| 7,176,466 B2 | 2/2007 | Rousso et al. |
| 7,187,790 B2 | 3/2007 | Sabol et al. |
| 7,217,953 B2 | 5/2007 | Carlson |
| 7,256,386 B2 | 8/2007 | Carlson et al. |
| 7,291,841 B2 | 11/2007 | Nelson et al. |
| 7,327,822 B2 | 2/2008 | Sauer et al. |
| 7,359,535 B2 | 4/2008 | Salla et al. |
| 7,373,197 B2 | 5/2008 | Daighighian et al. |
| 7,394,923 B2 | 7/2008 | Zou et al. |
| 7,444,010 B2 | 10/2008 | De Man |
| 7,468,513 B2 | 12/2008 | Charron et al. |
| 7,470,896 B2 | 12/2008 | Pawlak et al. |
| 7,490,085 B2 | 2/2009 | Walker et al. |
| 7,495,225 B2 | 2/2009 | Hefetz et al. |
| 7,502,499 B2 * | 3/2009 | Grady .................. 382/128 |
| 7,570,732 B2 | 8/2009 | Stanton et al. |
| 7,592,597 B2 | 9/2009 | Hefetz et al. |
| 7,620,444 B2 | 11/2009 | Le et al. |
| 7,627,084 B2 | 12/2009 | Jabri et al. |
| 7,652,259 B2 | 1/2010 | Kimchy et al. |
| 7,671,331 B2 | 3/2010 | Hefetz |
| 7,671,340 B2 | 3/2010 | Uribe et al. |
| 7,672,491 B2 * | 3/2010 | Krishnan et al. .............. 382/128 |
| 7,680,240 B2 | 3/2010 | Manjeshwar et al. |
| 7,705,316 B2 | 4/2010 | Rousso et al. |
| 7,734,331 B2 | 6/2010 | Dhawale et al. |
| 7,826,889 B2 | 11/2010 | David et al. |
| 7,831,024 B2 | 11/2010 | Metzler et al. |
| 7,835,927 B2 | 11/2010 | Schlotterbeck et al. |
| 7,872,235 B2 | 1/2011 | Rousso et al. |
| 7,894,650 B2 * | 2/2011 | Weng et al. .................... 382/128 |
| 7,968,851 B2 | 6/2011 | Rousso et al. |
| 8,013,308 B2 | 9/2011 | Guerin et al. |
| 8,055,329 B2 | 11/2011 | Kimchy et al. |
| 8,111,886 B2 | 2/2012 | Rousso et al. |
| 8,158,951 B2 | 4/2012 | Bal et al. |
| 8,163,661 B2 | 4/2012 | Akiyoshi et al. |
| 8,204,500 B2 | 6/2012 | Weintraub et al. |
| 8,338,788 B2 | 12/2012 | Zilberstein et al. |
| 8,440,168 B2 | 5/2013 | Yang et al. |
| 2001/0016029 A1 | 8/2001 | Tumer |
| 2001/0020131 A1 | 9/2001 | Kawagishi et al. |
| 2001/0035902 A1 | 11/2001 | Iddan et al. |
| 2001/0049608 A1 | 12/2001 | Hochman |
| 2002/0068864 A1 | 6/2002 | Bishop et al. |
| 2002/0072784 A1 | 6/2002 | Sheppard, Jr. et al. |
| 2002/0085748 A1 | 7/2002 | Baumberg |
| 2002/0087101 A1 | 7/2002 | Barrick et al. |
| 2002/0099295 A1 | 7/2002 | Gil et al. |
| 2002/0099310 A1 | 7/2002 | Kimchy et al. |
| 2002/0099334 A1 | 7/2002 | Hanson et al. |
| 2002/0103429 A1 | 8/2002 | DeCharms |
| 2002/0103431 A1 | 8/2002 | Toker et al. |
| 2002/0145114 A1 | 10/2002 | Inoue et al. |
| 2002/0148970 A1 | 10/2002 | Wong et al. |
| 2002/0165491 A1 | 11/2002 | Reilly |
| 2002/0168094 A1 * | 11/2002 | Kaushikkar et al. .......... 382/128 |
| 2002/0168317 A1 | 11/2002 | Daighighian et al. |
| 2002/0172405 A1 * | 11/2002 | Schultz .................. 382/128 |
| 2002/0179843 A1 | 12/2002 | Tanaka et al. |
| 2002/0183645 A1 | 12/2002 | Nachaliel |
| 2002/0188197 A1 | 12/2002 | Bishop et al. |
| 2002/0191734 A1 | 12/2002 | Kojima et al. |
| 2002/0198738 A1 | 12/2002 | Osborne |
| 2003/0001098 A1 | 1/2003 | Stoddart et al. |
| 2003/0001837 A1 | 1/2003 | Baumberg |
| 2003/0006376 A1 | 1/2003 | Tumer |
| 2003/0013950 A1 | 1/2003 | Rollo et al. |
| 2003/0013966 A1 | 1/2003 | Barnes et al. |
| 2003/0038240 A1 | 2/2003 | Weinberg |
| 2003/0055685 A1 | 3/2003 | Cobb et al. |
| 2003/0063787 A1 | 4/2003 | Natanzon et al. |
| 2003/0071219 A1 | 4/2003 | Motomura et al. |
| 2003/0081716 A1 | 5/2003 | Tumer |
| 2003/0135388 A1 | 7/2003 | Martucci et al. |
| 2003/0136912 A1 | 7/2003 | Juni |
| 2003/0144322 A1 | 7/2003 | Kozikowski et al. |
| 2003/0147887 A1 | 8/2003 | Wang et al. |
| 2003/0158481 A1 | 8/2003 | Stotzka et al. |
| 2003/0174804 A1 | 9/2003 | Bulkes et al. |
| 2003/0183226 A1 | 10/2003 | Brand et al. |
| 2003/0189174 A1 | 10/2003 | Tanaka et al. |
| 2003/0191430 A1 | 10/2003 | D'Andrea et al. |
| 2003/0202629 A1 | 10/2003 | Dunham et al. |
| 2003/0208117 A1 | 11/2003 | Shwartz et al. |
| 2003/0215122 A1 * | 11/2003 | Tanaka .................. 382/128 |
| 2003/0215124 A1 | 11/2003 | Li |
| 2003/0216631 A1 | 11/2003 | Bloch et al. |

(56) References Cited

U.S. PATENT DOCUMENTS

| | | | |
|---|---|---|---|
| 2003/0219149 A1* | 11/2003 | Vailaya et al. | 382/128 |
| 2004/0003001 A1 | 1/2004 | Shimura | |
| 2004/0010397 A1 | 1/2004 | Barbour et al. | |
| 2004/0015075 A1 | 1/2004 | Kimchy et al. | |
| 2004/0021065 A1 | 2/2004 | Weber | |
| 2004/0044282 A1 | 3/2004 | Mixon et al. | |
| 2004/0051368 A1 | 3/2004 | Caputo et al. | |
| 2004/0054248 A1 | 3/2004 | Kimchy et al. | |
| 2004/0054278 A1 | 3/2004 | Kimchy et al. | |
| 2004/0065838 A1 | 4/2004 | Tumer | |
| 2004/0075058 A1 | 4/2004 | Blevis et al. | |
| 2004/0081623 A1 | 4/2004 | Eriksen et al. | |
| 2004/0082918 A1 | 4/2004 | Evans et al. | |
| 2004/0084340 A1 | 5/2004 | Morelle et al. | |
| 2004/0086437 A1 | 5/2004 | Jackson et al. | |
| 2004/0101176 A1 | 5/2004 | Mendonca et al. | |
| 2004/0101177 A1* | 5/2004 | Zahlmann et al. | 382/128 |
| 2004/0116807 A1 | 6/2004 | Amrami et al. | |
| 2004/0120557 A1* | 6/2004 | Sabol et al. | 382/128 |
| 2004/0122311 A1 | 6/2004 | Cosman | |
| 2004/0125918 A1 | 7/2004 | Shanmugaval et al. | |
| 2004/0138557 A1 | 7/2004 | Le et al. | |
| 2004/0143449 A1 | 7/2004 | Behrenbruch et al. | |
| 2004/0144925 A1 | 7/2004 | Stoddart et al. | |
| 2004/0153128 A1 | 8/2004 | Suresh et al. | |
| 2004/0162492 A1* | 8/2004 | Kobayashi | 600/476 |
| 2004/0171924 A1 | 9/2004 | Mire et al. | |
| 2004/0183022 A1 | 9/2004 | Weinberg | |
| 2004/0184644 A1 | 9/2004 | Leichter et al. | |
| 2004/0193453 A1 | 9/2004 | Butterfield et al. | |
| 2004/0195512 A1 | 10/2004 | Crosetto | |
| 2004/0204646 A1 | 10/2004 | Nagler et al. | |
| 2004/0205343 A1 | 10/2004 | Forth et al. | |
| 2004/0210126 A1 | 10/2004 | Hajaj et al. | |
| 2004/0238743 A1 | 12/2004 | Gravrand et al. | |
| 2004/0251419 A1 | 12/2004 | Nelson et al. | |
| 2004/0253177 A1 | 12/2004 | Elmaleh et al. | |
| 2004/0258201 A1 | 12/2004 | Hayashida | |
| 2004/0263865 A1 | 12/2004 | Pawlak et al. | |
| 2005/0001170 A1 | 1/2005 | Juni | |
| 2005/0006589 A1 | 1/2005 | Young et al. | |
| 2005/0020898 A1 | 1/2005 | Vosniak et al. | |
| 2005/0020915 A1 | 1/2005 | Bellardinelli et al. | |
| 2005/0023474 A1 | 2/2005 | Persyk et al. | |
| 2005/0029277 A1 | 2/2005 | Tachibana | |
| 2005/0033157 A1 | 2/2005 | Klein et al. | |
| 2005/0049487 A1 | 3/2005 | Johnson et al. | |
| 2005/0055174 A1 | 3/2005 | David et al. | |
| 2005/0056788 A1 | 3/2005 | Juni | |
| 2005/0074402 A1 | 4/2005 | Cagnolini et al. | |
| 2005/0107698 A1 | 5/2005 | Powers et al. | |
| 2005/0107914 A1 | 5/2005 | Engleson et al. | |
| 2005/0108044 A1 | 5/2005 | Koster | |
| 2005/0113945 A1 | 5/2005 | Engleson et al. | |
| 2005/0113960 A1 | 5/2005 | Karau et al. | |
| 2005/0117029 A1 | 6/2005 | Shiomi | |
| 2005/0121505 A1 | 6/2005 | Metz et al. | |
| 2005/0131270 A1 | 6/2005 | Weil et al. | |
| 2005/0145797 A1 | 7/2005 | Oaknin et al. | |
| 2005/0148869 A1 | 7/2005 | Masuda | |
| 2005/0149350 A1 | 7/2005 | Kerr et al. | |
| 2005/0156115 A1 | 7/2005 | Kobayashi et al. | |
| 2005/0173643 A1 | 8/2005 | Tumer | |
| 2005/0187465 A1 | 8/2005 | Motomura et al. | |
| 2005/0198800 A1 | 9/2005 | Reich | |
| 2005/0203389 A1 | 9/2005 | Williams | |
| 2005/0205792 A1 | 9/2005 | Rousso et al. | |
| 2005/0205796 A1 | 9/2005 | Bryman | |
| 2005/0207526 A1 | 9/2005 | Altman | |
| 2005/0211909 A1 | 9/2005 | Smith | |
| 2005/0215889 A1 | 9/2005 | Patterson, II | |
| 2005/0234424 A1 | 10/2005 | Besing et al. | |
| 2005/0247893 A1 | 11/2005 | Fu et al. | |
| 2005/0253073 A1 | 11/2005 | Joram et al. | |
| 2005/0261936 A1 | 11/2005 | Silverbrook et al. | |
| 2005/0261937 A1 | 11/2005 | Silverbrook et al. | |
| 2005/0261938 A1 | 11/2005 | Silverbrook et al. | |
| 2005/0266074 A1 | 12/2005 | Zilberstein et al. | |
| 2005/0277833 A1 | 12/2005 | Williams, Jr. | |
| 2005/0277911 A1 | 12/2005 | Stewart et al. | |
| 2005/0278066 A1 | 12/2005 | Graves et al. | |
| 2005/0288869 A1 | 12/2005 | Kroll et al. | |
| 2006/0000983 A1 | 1/2006 | Charron et al. | |
| 2006/0033028 A1 | 2/2006 | Juni | |
| 2006/0036157 A1 | 2/2006 | Tumer | |
| 2006/0072799 A1 | 4/2006 | McLain | |
| 2006/0074290 A1 | 4/2006 | Chen et al. | |
| 2006/0104519 A1* | 5/2006 | Stoeckel et al. | 382/224 |
| 2006/0109950 A1 | 5/2006 | Arenson et al. | |
| 2006/0122503 A1 | 6/2006 | Burbank et al. | |
| 2006/0145081 A1 | 7/2006 | Hawman | |
| 2006/0160157 A1 | 7/2006 | Zuckerman | |
| 2006/0188136 A1* | 8/2006 | Ritt et al. | 382/128 |
| 2006/0214097 A1 | 9/2006 | Wang et al. | |
| 2006/0237652 A1 | 10/2006 | Kimchy et al. | |
| 2006/0257012 A1 | 11/2006 | Kaufman et al. | |
| 2007/0081700 A1* | 4/2007 | Blumenfeld et al. | 382/128 |
| 2007/0116170 A1 | 5/2007 | De Man et al. | |
| 2007/0133852 A1* | 6/2007 | Collins et al. | 382/128 |
| 2007/0156047 A1 | 7/2007 | Nagler et al. | |
| 2007/0166227 A1 | 7/2007 | Liu et al. | |
| 2007/0183582 A1 | 8/2007 | Baumann et al. | |
| 2007/0189436 A1 | 8/2007 | Goto et al. | |
| 2007/0194241 A1 | 8/2007 | Rousso et al. | |
| 2007/0265230 A1 | 11/2007 | Rousso et al. | |
| 2008/0001090 A1 | 1/2008 | Ben-Haim et al. | |
| 2008/0029704 A1 | 2/2008 | Hefetz et al. | |
| 2008/0033291 A1 | 2/2008 | Rousso et al. | |
| 2008/0036882 A1 | 2/2008 | Uemura et al. | |
| 2008/0039721 A1 | 2/2008 | Shai et al. | |
| 2008/0042067 A1 | 2/2008 | Rousso et al. | |
| 2008/0128626 A1 | 6/2008 | Rousso et al. | |
| 2008/0137938 A1* | 6/2008 | Zahniser | 382/133 |
| 2008/0230702 A1 | 9/2008 | Rousso et al. | |
| 2008/0230705 A1 | 9/2008 | Rousso et al. | |
| 2008/0237482 A1 | 10/2008 | Shahar et al. | |
| 2008/0260228 A1 | 10/2008 | Dichterman et al. | |
| 2008/0260580 A1 | 10/2008 | Helle et al. | |
| 2008/0260637 A1 | 10/2008 | Dickman | |
| 2008/0277591 A1 | 11/2008 | Shahar et al. | |
| 2009/0001273 A1 | 1/2009 | Hawman | |
| 2009/0018412 A1 | 1/2009 | Schmitt | |
| 2009/0078875 A1 | 3/2009 | Rousso et al. | |
| 2009/0112086 A1 | 4/2009 | Melman | |
| 2009/0152471 A1 | 6/2009 | Rousso et al. | |
| 2009/0190807 A1 | 7/2009 | Rousso et al. | |
| 2009/0201291 A1 | 8/2009 | Ziv et al. | |
| 2009/0236532 A1 | 9/2009 | Frach et al. | |
| 2009/0304582 A1 | 12/2009 | Rousso et al. | |
| 2010/0006770 A1 | 1/2010 | Balakin | |
| 2010/0021378 A1 | 1/2010 | Rousso et al. | |
| 2010/0102242 A1 | 4/2010 | Burr et al. | |
| 2010/0121184 A1 | 5/2010 | Dhawale et al. | |
| 2010/0140483 A1 | 6/2010 | Rousso et al. | |
| 2010/0202664 A1 | 8/2010 | Busch et al. | |
| 2010/0245354 A1 | 9/2010 | Rousso et al. | |
| 2012/0106820 A1 | 5/2012 | Rousso et al. | |
| 2012/0172699 A1 | 7/2012 | Nagler et al. | |
| 2012/0248320 A1 | 10/2012 | Wangerin et al. | |
| 2012/0326034 A1 | 12/2012 | Sachs et al. | |
| 2013/0051643 A1 | 2/2013 | Jackson et al. | |
| 2013/0114792 A1 | 5/2013 | Zilberstein et al. | |
| 2013/0308749 A1 | 11/2013 | Zilberstein et al. | |
| 2014/0151563 A1 | 6/2014 | Rousso et al. | |
| 2014/0163368 A1 | 6/2014 | Rousso et al. | |
| 2014/0187927 A1 | 7/2014 | Nagler et al. | |
| 2014/0193336 A1 | 7/2014 | Rousso et al. | |
| 2014/0200447 A1 | 7/2014 | Rousso et al. | |
| 2014/0249402 A1 | 9/2014 | Kimchy et al. | |

FOREIGN PATENT DOCUMENTS

| | | |
|---|---|---|
| DE | 19815362 | 10/1999 |
| EP | 0273257 | 7/1988 |

(56) References Cited

FOREIGN PATENT DOCUMENTS

| | | |
|---|---|---|
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 06-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 6/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | WO 00/25268 | 5/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO 2004/042546 | 5/2004 |
| WO | WO 2004/113951 | 12/2004 |
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

Appeal Brief Dated Jan. 19, 2010 to Notice of Appeal of Nov. 16, 2009 From the US Patent and Trademark Office Re.: U.S. Appl. No. 10/616,301.
Communication Pursuant to Article 93(3) EPC Dated Mar. 8, 2010 From the European Patent Office Re.: Application No. 06832278.3.
Communication Pursuant to Article 94(3) EPC Dated Mar. 8, 2010 From the European Patent Office Re.: Application No. 06832278.3.
Communication Pursuant to Article 94(3) EPC Dated May 12, 2010 From the European Patent Office Re.: Application No. 06809851.6.
Communication Pursuant to Article 94(3) EPC Dated Apr. 16, 2010 From the European Patent Office Re. Application No. 01951883.6.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
International Preliminary Report on Patentability Dated Apr. 16, 2009 From the International Bureau of WIPO Re.: Application No. PCT/IL2007/000918.
International Preliminary Report on Patentability Dated Jun. 21, 2007 From the International Bureau of WIPO Re.: Application No. PCT/IL2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 10, 2006 From the International Searching Authority of the Patent Cooperation Treaty Re.: Application No. PCT/IL06/00059.
International Search Report Dated Jul. 11, 2008 From the International Searching Authority of the Patent Cooperation Treaty Re.: Application No. PCT/IL06/01511.
International Search Report Dated Jul. 25, 2008 From the International Searching Authority of the Patent Cooperation Treaty Re.: Application No. PCT/IL2007/001588.
International Search Report Dated Feb. 1, 2006 From the International Searching Authority of the Patent Cooperation Treaty Re.: Application No. PCT/IL05/00048.
International Search Report Dated Jul. 1, 2008 From the International Searching Authority of the Patent Cooperation Treaty Re.: Application No. PCT/IL06/00834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Aug. 3, 2006 From the international Searching Authority of the Patent Cooperation Treaty Re.: Application No. PCT/IL05/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.

(56) References Cited

OTHER PUBLICATIONS

International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.
International Search Report Dated Mar. 23, 2006 From the International Searching Authority of the Patent Cooperation Treaty Re.: Application No. PCT/IL05/00572.
International Search Report Dated May 24, 2007 From the International Searching Authority of Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Jul. 16, 2009 From the US Patent and Trademark Office Re.: U.S. Appl. No. 12/084,559.
Notice of Allowance Dated Sep. 17, 2009 From the US Patent and Trademark Office Re.: U.S. Appl. No. 10/533,568. Suppl. IDS VIII in 25855.
Notice of Allowance Dated Jul. 22, 2010 From the US Patent and Trademark Office Re.: U.S. Appl. No. 11/794,799.
Notice of Allowance Dated Nov. 23, 2009 From the US Patent and Trademark Office Re.: U.S. Appl. No. 12/084,559.
Notice of Allowance Dated Aug. 25, 2010 From the US Patent and Trademark Office Re. U.S. Appl. No. 11/980,617.
Notice of Allowance Dated Jun. 30, 2010 From the United States Patent and Trademark Office Re.: U.S. Appl. No. 09/727,464.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Aug. 3, 2010 From the US Patent and Trademark Office Re.: U.S. Appl. No. 11/980,690.
Official Action Dated May 3, 2007 From the US Patent and Trademark Office Re.: U.S. Appl. No. 10/240,239.
Official Action Dated Sep. 4, 2008 From the US Patent and Trademark Office Re.: U.S. Appl. No. 10/533,568.
Official Action Dated Sep. 5, 2002 From the US Patent and Trademark Office Re.: U.S. Appl. No. 12/084,559.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Oct. 7, 2008 From the US Patent and Trademark Office Re.: U.S. Appl. No. 10/616,301.
Official Action Dated Apr. 8, 2010 From the US Patent and Trademark Office Re.: U.S. Appl. No. 11/980,690.
Official Action Dated Dec. 8, 2009 From the US Patent and Trademark Office Re.: U.S. Appl. No. 11/132,320.
Official Action Dated Jan. 8, 2010 From the US Patent and Trademark Office Re.: U.S. Appl. No. 11/656,548.
Official Action Dated Apr. 9, 2010 From the US Patent and Trademark Office Re.: U.S. Appl. No. 11/798,017.
Official Action Dated Aug. 10, 2007 From the US Patent and Trademark Office Re.: U.S. Appl. No. 10/836,223.
Official Action Dated Aug. 11, 2009 From the US Patent and Trademark Office Re.: U.S. Appl. No. 09/641,973.
Official Action Dated Mar. 11, 2010 From the US Patent and Trademark Office Re.: U.S. Appl. No. 11/607,075.
Official Action Dated Jul. 12, 2007 From the US Patent and Trademark Office Re.: U.S. Appl. No. 10/616,301.
Official Action Dated Dec. 13, 2007 From the US Patent and Trademark Office Re.: U.S. Appl. No. 10/616,301.
Official Action Dated May 13, 2009 From the US Patent and Trademark Office Re.: U.S. Appl. No. 11/798,017.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Jul. 15, 2009 From the US Patent and Trademark Office Re.: U.S. Appl. No. 10/616,301.
Official Action Dated Mar. 15, 2004 From the US Patent and Trademark Office Re.: U.S. Appl. No. 09/765,316.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Sep. 16, 2009 From the US Patent and Trademark Office Re.: U.S. Appl. No. 09/727,464.
Official Action Dated Jan. 17, 2006 From the United States Patent and Trademark Office Re.: U.S. Appl. No. 11/034,007.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Jul. 20, 2009 From the US Patent and Trademark Office Re.: U.S. Appl. No. 11/980,617.
Official Action Dated Mar. 21, 2008 From the US Patent and Trademark Office Re.: U.S. Appl. No. 10/533,568.
Official Action Dated Sep. 21, 2009 From the US Patent and Trademark Office Re.: U.S. Appl. No. 11/798,017.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.

(56) References Cited

OTHER PUBLICATIONS

Official Action Dated Jun. 23, 2006 From the United States Patent and Trademark Office Re.: U.S. Appl. No. 09/727,464.
Official Action Dated Jun. 25, 2008 From the US Patent and Trademark Office Re.: U.S. Appl. No. 10/616,301.
Official Action Dated Sep. 25, 2006 From the US Patent and Trademark Office Re.: U.S. Appl. No. 10/616,301.
Official Action Dated Nov. 26, 2008 From the US Patent and Trademark Office Re.: U.S. Appl. No. 10/240,239.
Official Action Dated Jul. 27, 2010 From the US Patent and Trademark Office Re.: U.S. Appl. No. 10/616,307.
Official Action Dated Apr. 28, 2010 From the US Patent and Trademark Office Re.: U.S. Appl. No. 10/616,301.
Official Action Dated Aug. 28, 2009 From the US Patent and Trademark Office Re.: U.S. Appl. No. 10/240,239.
Official Action Dated Apr. 29, 2009 From the US Patent and Trademark Office Re.: U.S. Appl. No. 11/980,690.
Official Action Dated Oct. 30, 2009 From the US Patent and Trademark Office Re.: U.S. Appl. No. 11/980,690.
Official Action Dated Sep. 30, 2008 From the US Patent and Trademark Office Re.: U.S. Appl. No. 10/616,301.
Official Action Dated Sep. 30, 2010 From the US Patent and Trademark Office Re.: U.S. Appl. No. 11/798,017.
Response Dated Jul. 1, 2010 to Official Action of Mar. 2, 2010 From the US Patent and Trademark Office Re.: U.S. Appl. No. 10/836,223.
Response Dated Jul. 1, 2010 to Official Action of Mar. 2, 2010 From the US Patent and Trademark Office Re.: U.S. Appl. No. 11/980,617.
Response Dated Jun. 1, 2010 to Official Action of Mar. 1, 2010 From the US Patent and Trademark Office Re.: U.S. Appl. No. 11/794,799.
Response dated Sep. 1, 2010 to Official Action of Aug. 3, 2010 From the US Patent and Trademark Office Re.: U.S. Appl. No. 11/980,690.
Response Dated Jun. 3, 2010 to Notice of Appeal and Pre-Appeal Brief of Jan. 4, 2010 to Official Action of Sep. 2, 2009 From the US Patent and Trademark Office Re.: U.S. Appl. No. 10/343,792.
Response Dated Oct. 5, 2010 to Official Action of Jul. 19, 2010 From the US Patent and Trademark Office Re.: U.S. Appl. No. 11/656,548.
Response Dated Apr. 7, 2009 to Official Action of Oct. 7, 2008 From the US Patent and Trademark Office Re.: U.S. Appl. No. 10/616,301.
Response Dated Jul. 8, 2010 to Communication Pursuant to Article 94(3) EPC of Mar. 8, 2010 From the European Patent Office Re.: Application No. 06832278.3.
Response Dated Jul. 8, 2010 to Official Action of Apr. 9, 2010 From the US Patent and Trademark Office Re.: U.S. Appl. No. 11/798,017.
Response Dated Sep. 8, 2010 to Communication Pursuant to Article 94(3) EPC Dated May 12, 2010 From the European Patent Office Re.: Application No. 06809851.6.
Response Dated Dec. 10, 2009 to Official Action of Aug. 11, 2009 From the US Patent and Trademark Office Re.: U.S. Appl. No. 09/641,973.
Response Dated May 10, 2010 to Official Action of Apr. 8, 2010 From the US Patent and Trademark Office Re.: U.S. Appl. No. 11/980,690.
Response Dated May 10, 2010 to Official Action of Jan. 8, 2010 From the US Patent and Trademark Office Re.: U.S. Appl. No. 11/656,548.
Response Dated May 11, 2010 to Official Action of Mar. 11, 2010 From the US Patent and Trademark Office Re.: U.S. Appl. No. 11/607,075.
Response Dated Oct. 12, 2009 to Notice of Allowance of Jul. 16, 2009 From the US Patent and Trademark Office Re.: U.S. Appl. No. 12/084,559.
Response Dated Mar. 13, 2008 to Official Action of Dec. 13, 2007 From the US Patent and Trademark Office Re.: U.S. Appl. No. 10/616,301.
Response Dated Aug. 14, 2008 to Official Action of Apr. 15, 2008 From the US Patent and Trademark Office Re.: U.S. Appl. No. 09/727,464.
Response Dated Jan. 14, 2010 to Official Action of Sep. 15, 2009 From the US Patent and Trademark Office Re.: U.S. Appl. ,No. 10/616,307.
Response Dated Jan. 14, 2010 to Official Action of Sep. 15, 2009 From the US Patent and Trademark Office Re.: U.S. Appl. No. 10/836,223.
Response Dated Oct. 14, 2009 to Official Action of May 14, 2009 From the US Patent and Trademark Office Re.: U.S. Appl. No. 11/656,548.
Response Dated Mar. 15, 2007 to Official Action of Dec. 15, 2006 From the US Patent and Trademark Office Re.: U.S. Appl. No. 10/616,301.
Response Dated Aug. 16, 2010 to Communication Pursuant to Article 94(3) EPC of Apr. 16, 2010 From the European Patent Office Re. Application No. 01951883.6.
Response Dated Jan. 21, 2010 to Official Action of Sep. 21, 2009 From the US Patent and Trademark Office Re.: U.S. Appl. No. 11/798,017.
Response Dated Feb. 22, 2010 to Communication Pursuant to Article 94(3) EPC of Oct. 21, 2009 From the European Patent Office Re.: Application No. 02716285.8.
Response Dated Sep. 22, 2008 to Official Action of Jun. 25, 2008 From US Patent and Trademark Office Re.: U.S. Appl. No. 10/616,301.
Response Dated Jun. 23, 2010 to Official Action of Feb. 23, 2010 From the US Patent and Trademark Office Re.: U.S. Appl. No. 09/641,973.
Response Dated Aug. 25, 2010 to Official Action of Jul. 27, 2010 From the US Patent and Trademark Office Re.: U.S. Appl. No. 10/616,307.
Response Dated Nov. 25, 2005 to Office Action of May 13, 2005 From the Patent Office of the People's Republic of China Re.: Application No. 1817689.5.
Response Dated Jul. 26, 2010 to Official Action of Apr. 28, 2010 From the US Patent and Trademark Office Re.: U.S. Appl. No. 10/616,301.
Response Dated May 26, 2010 to Official Action of Mar. 19, 2010 From the US Patent and Trademark Office Re.: U.S. Appl. No. 10/240,239.
Response Dated Dec. 28, 2009 to Official Action of Aug. 28, 2009 From the US Patent and Trademark Office Re.: U.S. Appl. No. 10/240,239.
Response Dated Dec. 30, 2009 to Official Action of Sep. 1, 2009 From the US Patent and Trademark Office Re.: U.S. Appl. No. 11/794,799.
Response Dated Dec. 30, 2009 to Official Action of Oct. 30, 2009 From the US Patent and Trademark Office Re.: U.S. Appl. No. 11/980,690.
Response Dated Oct. 31, 2007 to Official Action of Jul. 12, 2007 From the US Patent and Trademark Office Re.: U.S. Appl. No. 10/616,301.
Response to the International Search Report and the Written Opinion of Oct. 10, 2006 From the International Searching Authority Re.: Appliction No. PCT/IL06/00059.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplemental Response After Interview Dated Aug. 4, 2010 to Official Action of Mar. 2, 2010 From the US Patent and Trademark Office Re.: U.S. Appl. No. 11/980,617.
Supplemental Response Under 37 C.F.R. § 1.125 Dated Aug. 12, 2010 to Telephonic Interview of Aug. 6, 2010 From the US Patent and Trademark Office Re. U.S. Appl. No. 11/980,617.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Supplementary Partial European Search Report Dated Sep. 4, 2007 From the European Patent Office Re.: Application No. 0 2716285.8.

(56) References Cited

OTHER PUBLICATIONS

Supplementary Partial European Search Report Dated Nov. 11, 2008 From the European Patent Office Re.: Application No. 01951883.6.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Jul. 2, 2007 From the International Searching Authority of the Patent Cooperation Treaty Re.: Application No. PCT/IL2006/001291.
Written Opinion Dated Aug. 3, 2006 From the International Searching Authority of the Patent Cooperation Treaty Re.: Application No. PCT/IL05/001173.
Written Opinion Dated Oct. 10, 2006 From the International Searching Authority of the Patent Cooperation Treaty Re.: Application No. PCT/IL06/00059.
Written Opinion Dated Oct. 15, 2008 From the International Searching Authority Re.: Application No. PCT/IL07/00918.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Aoi et al. "Absolute Quantitation of Regional Myocardial Blood Flow of Rats Using Dynamic Pinhole SPECT", IEEE Nuclear Science Symposium and Medical Imaging Conference Record, 3: 1780-1783, 2002. Abstract, Figs.
Beekman et al. "Efficient Fully 3-D iterative SPECT Reconstruction With Monte Carlo-Based Scatter Compensation", IEEE Transactions on Medical Imaging, 21(8): 867-877, Aug. 2002.
Bloch et al. "Application of Computerized Tomography to Radiation Therapy and Surgical Planning", Proceedings of the IEEE, 71(3): 351-355, Mar. 1983.
Bromiley et al. "Attenuation Correction in PET Using Consistency Conditions and a Three-Dimensional Template", IEEE Transactions on Nuclear Science, XP002352920, 48(4): 1371-1377, 2001. p. 1376, col. 2, § 2.
Brown et al. "Method for Segmenting Chest CT Image Data Using an Anatomical Model: Preliminary Results", IEEE Transactions on Medical Imaging, 16(6): 828-839, Dec. 1997.
Corstens et al. "Nuclear Medicine's Role in Infection and Inflammation", The Lancet, 354: 765-770, 1999.
Day et al. "Localization of Radioiodinated Rat Fibrogen in Transplanted Rat Tumors", Journal of the National Cancer Institute, 23(4): 799-812, 1959.
Del Guerra et al. "An Integrated PET-SPECT Small Animal Imager: Preliminary Results", Nuclear Science Symposium, IEEE Records, 1: 541-544, 1999.
Erbil et al. "Use and Limitations of Serum Total and Lipid-Bound Sialic Acid Concentrations as Markers for Colorectal Cancer", Cancer, 55: 404-409, 1985.
Garcia et al. "Accuracy of Dynamic SPECT Acquisition for Tc-99m Teboroxime Myocardial Perfusion Imaging: Preliminary Results", American College of Cardiology, 51st Annual Scientific Session, Atlanta, Georgia, USA, 8 P., 2002.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Gugnin et al "Radiocapsule for Recording the Ionizing Radiation in the Gastrointestinal Tract", UDC 615. 417:616.34-005.1-073.916-71 (All-Union Scientific-Research Institute of medical Instrument Design, Moscow. Translated from Meditsinskaya Tekhnika, 1:21-25, Jan.-Feb. 1972).
Hassan et al. "A Radiotelemetry Pill for the Measurement of Ionising Radiation Using a Mercuric Iodide Detector", Physics in Medicine and Biology, 23(2): 302-308, 1978.
Hayakawa et al. "A PET-MRI Registration Technique for PET Studies of the Rat Brain", Nuclear Medicine & Biology, 27: 121-125, 2000. p. 121, col. 1.
Hoffman et al. "Intraoperative Probes and Imaging Probes", European Journal of Nuclear Medicine, 26(8): 913-935, 1999.
Huesman et al. "Kinetic Parameter Estimation From SPECT Cone-Beam Projection Measurements", Physics in Medicine and Biology, 43(4): 973-982, 1998.
Jeanguillaume et al. "From the Whole-Body Counting to Imaging: The Computer Aided Collimation Gamma Camera Project (CACAO)", Radiation Projection Dosimetry 89(3-4): 349-352, 2000.
Jessup "Tumor Markers—Prognostic and Therapeutic Implications for Colorectal Carcinoma", Surgical Oncology, 7: 139-151, 1998.
Kadrmas et al. "Static Versus Dynamic Teboroxime Myocardial Perfusion SPECT in Canines", IEEE Transactions on Nuclear Sicence, 47(3): 1112-1117, Jun. 2000.
Kinahan et al. "Attenuation Correction for a Combined 3D PET/CT Scanner", Medical Physics, 25(10): 2046-2053, Oct. 1998.
Kojima et al. "Quantitative Planar Imaging Method for Measurement of Renal Activity by Using a Conjugate-Emission Image and Transmission Data", Medical Physics, 27(3): 608-615, 2000. p. 608.
Lavallée et al. "Building a Hybrid Patient's Model for Augmented Reality in Surgery: A Registration Problem", Computing in Biological Medicine, 25(2): 149-164, 1995.
Li et al. "A HOTLink/Networked PC Data Acquisition and Image Reconstruction System for a High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., 2nd §.
Molinolo et al. "Enhanced Tumor Binding Using Immunohistochemical Analyses by Second Generation Anti-Tumor-Associated Glycoprotein 72 Monoclonal Antibodies versus Monoclonal Antibody B72.3 in Human Tissue", Cancer Research, 50: 1291-1298, 1990.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Mori et al. "Overexpression of Matrix Metalloproteinase-7mRNA in Human Colon Carcinomas", Cancer, 75: 1516-1519, 1995.
Ogawa et al. "Ultra High Resoultion Pinhole SPECT", IEEE Nuclear Science Symposium, 2: 1600-1604, 1998.
Pardridge et al. "Tracer Kinetic Model of Blood-Brain Barrier Transport of Plasma Protein-Bound Ligands", Journal of Clinical Investigation, 74: 745-752, 1984. Suppl. IDS in 27480.
Pellegrini et al. "Design of Compact Pinhole SPECT System Based on Flat Panel PMT", IEEE Nuclear Science Symposium Conference Record, 3: 1828-1832, 2003.
Piperno et al. "Breast Cancer Screening by Impedance Measurements", Frontiers Med. Biol. Engng., 2(2): 11-17, 1990.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.

(56) References Cited

OTHER PUBLICATIONS

Quartuccia et al. "Computer Assisted Collimation Gama Camera: A New Approach to Imaging Contaminated Tissues", Radiation Projection Dosimetry, 89(3-4): 343-348, 2000.
Rajshekhar "Continuous Impedence Monitoring During CT-Guided Stereotactic Surgery: Relative Value in Cystic and Solid Lesions", British Journal of Neurosurgery, 6: 439-444, 1992.
Reutter et al. "Direct Least Squares Estimation of Spatiotemporal Distributions From Dynamic SPECT Projections Using a Spatial Segmentation and Temporal B-Splines", IEEE Transactions on Medical Imaging, 19(5): 434-450, 2000.
Reutter et al. "Kinetic Parameter Estimation From Attenuated SPECT Projection Measurements", IEEE Transactions on Nuclear Science, 45(6): 3007-3013, 1998.
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2—p. 585, § 1.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Wu et al. "ECG-Gated Pinhole SPECT in Mice With Millimeter Spatial Resolution", IEEE Transactions on Nuclear Science, 47(3): 1218-1221, Jun. 2000.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Zhang et al. "An Innovative High Efficiency and High Resolution Probe for Prostate Imaging", The Journal of Nuclear Medicine, 68: 18, 2000. Abstract.
Official Action Dated Dec. 15, 2011 From the US Patent and Trademark Office Re.: U.S. Appl. No. 10/343,792.
Official Action Dated Dec. 20, 2011 From the US Patent and Trademark Office Re. U.S. Appl. No. 12/309,479.
Response Dated Nov. 13, 2011 to Official Action of Sep. 12, 2011 From the US Patent and Trademark Office Re. U.S. Appl. No. 11/980,653.
Response Dated Dec. 29, 2011 to Office Action of Jul. 17, 2007 From the Israeli Patent Office Re.: Application No. 154323.
Berman et al. "Dual-Isotope Myocardial Perfusion SPECT With Rest Thallium-201 and Stress Tc-99m Sestamibi", Cardiology Clinics, 12(2): 261-270, May 1994.
DeGrado et al. "Topics in Integrated Systems Physiology. Tracer Kinetic Modeling in Nuclear Cardiology", Journal of Nuclear Cardiology, 7: 686-700, 2000.
Links "Advances in SPECT and PET Imaging", Annals in Nuclear Medical Science, 13(2): 107-120, Jun. 2000.
Official Action Dated Dec. 8, 2010 From the US Patent and Trademark Office Re.: U.S. Appl. No. 11/980,690.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Nov. 23, 2010 From the US Patent and Trademark Office Re.: U.S. Appl. No. 11/656,548.
Response Dated Nov. 18, 2010 to Official Action of Jul. 19, 2010 From the US Patent and Trademark Office Re.: U.S. Appl. No. 11/607,075.
Notice of Allowance Dated Dec. 17, 2010 From the US Patent and Trademark Office Re. U.S. Appl. No. 11/980,617.
Official Action Dated Dec. 8, 2010 From the US Patent and Trademark Office Re.: U.S. Appl. No. 09/641,973.
Official Action Dated Dec. 28, 2010 From the US Patent and Trademark Office Re.: U.S. Appl. No. 11/607,075.
Response Dated Dec. 15, 2010 to Official Action of Jul. 19, 2010 From the US Patent and Trademark Office Re.: U.S. Appl. No. 11/656,548.
Official Action Dated Oct. 7, 2011 From the US Patent and Trademark Office Re. U.S. Appl. No. 11/750,057.
Official Action Dated Oct. 7, 2011 From the US Patent and Trademark Office Re. U.S. Appl. No. 11/932,872.
Official Action Dated Jan. 19, 2012 From the US Patent and Trademark Office Re. U.S. Appl. No. 11/667,793.
Official Action Dated Jan. 23, 2012 From the US Patent and Trademark Office Re. U.S. Appl. No. 12/087,150.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Toennies et al. "Scatter Segmentation in Dynamic SPECT Images Using Principal Component Analysis", Progress in Biomedical Optics and Imaging, 4(23): 507-516, 2003.
Communication Pursuant to Article 94(3) EPC Dated Sep. 23, 2011 From the European Patent Office Re.: Application No. 06832278.3.
Written Opinion Dated Nov. 1, 2007 from the International Searching Authority of the Patent Cooperation Treaty Re.: Application No. PCT/IL06/00840.
Written Opinion Dated Jul. 11, 2008 from the International Searching Authority of the Patent Cooperation Treaty Re.: Application No. PCT/IL06/01511.
Official Action Dated Jan. 31, 2011 From the US Patent and Trademark Office Re. U.S. Appl. No. 11/667,793.
Official Action Dated Jan. 28, 2011 From the US Patent and Trademark Office Re.: U.S. Appl. No. 09/641,973.
Response Dated Feb. 10, 2011 to Official Action of Nov. 10, 2010 From the US Patent and Trademark Office Re.: U.S. Appl. No. 10/616,307.
Response Dated Jan. 27, 2011 to Official Action of Nov. 1, 2010 From the US Patent and Trademark Office Re.: U.S. Appl. No. 11/980,690.
Response Dated Jan. 31, 2011 to Official Action of Sep. 30, 2010 From the US Patent and Trademark Office Re.: U.S. Appl. No. 11/798,017.
Notice of Allowance Dated Feb. 2, 2012 From the US Patent and Trademark Office Re. U.S. Appl. No. 11/628,074.
Communication Pursuant to Article 94(3) EPC Dated Mar. 2, 2011 From the European Patent Office Re.: Application No. 06756259.5.
Notice of Allowance Dated Nov. 15, 2010 From the US Patent and Trademark Office Re. U.S. Appl. No. 10/616,301.
Notice of Non-Compliant Amendment Dated Feb. 14, 2011 From the US Patent and Trademark Office Re.: U.S. Appl. No. 10/616,307.
Response Dated Feb. 10, 2011 to Notice of Allowance of Nov. 15, 2010 From the US Patent and Trademark Office Re. U.S. Appl. No. 10/616,301.
Mettler et al. "Legal Requirements and Radiation Safely", Essentials of Nuclear Medicine Imaging, 2nd Ed., Chap.13: 323-331, 1985.
Notice of Panel Decision From Pre-Appeal Brief Review Dated Feb. 29, 2012 From the US Patent and Trademark Office Re.: U.S. Appl. No. 10/836,223.
Official Action Dated Mar. 1, 2012 From the US Patent and Trademark Office Re.: U.S. Appl. No. 10/616,307.
Official Action Dated Dec. 22, 2011 From the US Patent and Trademark Office Re. U.S. Appl. No. 12/514,785.
Official Action Dated Feb. 28, 2012 From the US Patent and Trademark Office Re.: U.S. Appl. No. 09/641,973.
International Search Report Dated May 24, 2007 From the International Searching Authority of the Patent Cooperation Treaty Re.: Application No. PCT/IL05/00575.
Response Dated Mar. 8, 2011 to Official Action of Dec. 8, 2010 From the US Patent and Trademark Office Re.: U.S. Appl. No. 11/980,690.
Lavall?e et al. "Building a Hybrid Patient's Model for Augmented Reality in Surgery: A Registration Problem", Computing in Biological Medicine, 25(2): 149-164, 1995.

(56) References Cited

OTHER PUBLICATIONS

Lin et al. "Improved Sensor Pills for Physiological Monitoring", NASA Technical Brief, JPL New Technology Report, NPO-20652, 25(2), 2000.
Mettler et al. "Legal Requirements and Radiation Safety", Essentials of Nuclear Medicine Imaging, 2nd Ed., Chap.13: 323-331, 1985.
Notice of Allowance Dated Feb. 23, 2011 From the US Patent and Trademark Office Re.: U.S. Appl. No. 11/980,690.
Official Action Dated Mar. 15, 2011 From the US Patent and Trademark Office Re.: U.S. Appl. No. 10/343,792.
Response Dated Mar. 24, 2011 to Official Action of Dec. 8, 2010 From the US Patent and Trademark Office Re.: U.S. Appl. No. 09/641,973.
Official Action Dated Mar. 6, 2012 From the US Patent and Trademark Office Re. U.S. Appl. No. 12/792,856.
Restriction Official Action Dated Mar. 9, 2012 From the US Patent and Trademark Office Re. U.S. Appl. No. 11/976,852.
Office Action Dated Jul. 17, 2007 From the Israeli Patent Office Re.: Application No. 154323 and Its Translation Into English.
Communication Pursuant to Rules 70(2) and 70a(2) EPC Dated Apr. 4, 2011 From the European Patent Office Re. Application No. 05803689.8.
Response Dated Mar. 31, 2011 to Official Action of Jan. 31, 2011 From the US Patent and Trademark Office Re. U.S. Appl. No. 11/667,793.
Response Dated Apr. 5, 2011 to Official Action of Nov. 10, 2010 From the US Patent and Trademark Office Re.: U.S. Appl. No. 10/836,223.
Supplementary European Search Report and the European Search Opinion Dated Mar. 16, 2011 From the European Patent Office Re. Application No. 05803689.8.
Hermann et al. "Mitochondrial Proteome: Altered Cytochtrome C Oxidase Subunit Levels in Prostate Cancer", Proteomics, XP002625778, 3(9): 1801-1810, Sep. 2003.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Interview Summary Dated Mar. 25, 2011 From the US Patent and Trademark Office Re.: U.S. Appl. No. 10/836,223.
Mao et al. "Human Prostatic Carcinoma: An Electron Microscope Study", Cancer Research, XP002625777, 26(5): 955-973, May 1966.
Storey et al. "TC-99m Sestamibi Uptake in Metastatic Prostate Carcinoma", Clinical Nuclear Medicine, XP009145398, 25(2): 133-134, Feb. 2000.
Restriction Official Action Dated Apr. 13, 2012 From the US Patent and Trademark Office Re. U.S. Appl. No. 11/989,223.
Response Dated Mar. 3, 2011 to Notice of Non-Compliant Amendment of Feb. 14, 2011 From the US Patent and Trademark Office Re.: U.S. Appl. No. 10/616,307.
Response Dated Jan. 14, 2010 to Official Action of Sep. 15, 2009 From the US Patent and Trademark Office Re.: U.S. Appl. No. 10/616,307.
Kadrmas et al. "Static Versus Dynamic Teboroxime Myocardial Perfusion SPECT in Canines", IEEE Transactions on Nuclear Science, 47(3): 1112-1117, Jun. 2000.
International Preliminary Report on Patentability Dated Apr. 16, 2009 From the International Bureau of WIPO Re.: Applicaiton No. PCT/IL2007/000918.
International Search Report May 24, 2007 From the International Searching Authority of the Patent Cooperation Treaty Re.: Application No. PCT/IL05/00575.
Invitation to Pay Additional Fees Dated Feb. 15, 2007, From the International Searching Authority Re.: Application No. PCT/IL05/00575.
Office Action Dated Sep. 4, 2007, From the Israeli Patent Office Re.: Application No. 157007.
Official Action Dated Jun. 1, 2006, From the United States Patent and Trademark Office Re.: U.S. Appl. No. 10/686,536.
Official Action Dated May 3, 2007 From the United States Patent and Trademark Office Re.: U.S. Appl. No. 10/240,239.

Official Action Dated Sep. 5, 2002 From the United States Patent and Trademark Office Re.: U.S. Appl. No. 12/084,559.
Official Action Dated Oct. 7, 2008 From the US Patent Office Re.: U.S. Appl. No. 10/616,301.
Official Action Dated Aug. 10, 2007 From the United States Patent and Trademark Office Re.: U.S. Appl. No. 10/836,223.
Official Action Dated Apr. 15, 2008 From the United States Patent and Trademark Office Re.: U.S. Appl. No. 09/641,973.
Official Action Dated Dec. 15, 2006 From the US Patent Office Re.: U.S. Appl. No. 10/616,301.
Official Action Dated Feb. 15, 2008 From the United States Patent and Trademark Office Re.: U.S. Appl. No. 10/343,792.
Official Action Dated Jul. 15, 2008 From the United States Patent and Trademark Office Re.: U.S. Appl. No. 09/641,973.
Official Action Dated Mar. 15, 2004 From the United States Patent and Trademark Office Re.: U.S. Appl. No. 09/725,316.
Second Written Opinion Dated Jun. 1, 2009 From the International Searching Authority Re.: Application No. PCT/IL07/00918.
Stoddart et al. "New Multi-Dimensional Reconstructions for the 12-Detector, Scanned Focal Point, Single-Photon Tomograph", Physics in Medicine and Biology, XP020021960, 37(3): 579-586, Mar. 1, 1992. p. 582, § 2-p. 585, § 1.
Notice of Allowance Dated Sep. 17, 2009 From the US Patent and Trademark Office Re.: U.S. Appl. No. 10/533,568.
Response Dated Nov. 16, 2009 to Official Action of Jul. 15, 2009 From the US Patent and Trademark Office Re.: U.S. Appl. No. 10/616,301.
Response Dated Apr. 18, 2010 to Official Action of Feb. 17, 2010 From the US Patent and Trademark Office Re.: U.S. Appl. No. 11/702,154.
Official Action Dated Apr. 16, 2012 From the US Patent and Trademark Office Re.: U.S. Appl. No. 10/836,223.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Official Action Dated Apr. 20, 2011 From the US Patent and Trademark Office Re.: U.S. Appl. No. 11/798,017.
Official Action Dated Apr. 27, 2011 From the US Patent and Trademark Office Re.: U.S. Appl. No. 10/836,223.
Communication Pursuant to Article 94(3) EPC Dated May 12, 2010 From the European Patent Office Re. Application No. 06809851.6.
International Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Search Report Dated Jul. 1, 2008 From the International Searching Authority Re. Application No. PCT/IL2006/000834.
International Search Report Dated Jul. 2, 2007 From the International Searching Authority Re. Application No. PCT/IL2006/001291.
International Search Report Dated Aug. 3, 2006 From the International Searching Authority Re. Application No. PCT/IL2005/001173.
International Search Report Dated Oct. 15, 2008 From the International Searching Authority Re. Application No. PCT/2007/000918.
Official Action Dated Nov. 1, 2010 From the US Patent and Trademark Office Re. U.S. Appl. No. 12/728,383.
Official Action Dated Mar. 2, 2010 From the US Patent and Trademark Office Re. U.S. Appl. No. 11/980,617.
Official Action Dated Dec. 8, 2010 From the US Patent and Trademark Office Re. U.S. Appl. No. 11/980,690.
Official Action Dated Apr. 9, 2010 From the US Patent and Trademark Office Re. U.S. Appl. No. 11/798,017.
Official Action Dated Aug. 13, 2008 From the US Patent and Trademark Office Re. U.S. Appl. No. 11/769,826.

(56) References Cited

OTHER PUBLICATIONS

Official Action Dated Feb. 16, 2012 From the US Patent and Trademark Office Re. U.S. Appl. No. 11/747,378.
Official Action Dated May 18, 2012 From the US Patent and Trademark Office Re. U.S. Appl. No. 11/989,223.
Official Action Dated Apr. 20, 2011 From the US Patent and Trademark Office Re. U.S. Appl. No. 11/798,017.
Official Action Dated Sep. 21, 2009 From the US Patent and Trademark Office Re. U.S. Appl. No. 11/798,017.
Official Action Dated May 23, 2011 From the US Patent and Trademark Office Re. U.S. Appl. No. 11/980,690.
Official Action Dated Sep. 30, 2010 From the US Patent and Trademark Office Re. U.S. Appl. No. 11/798,017.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Pharmalucence "Kit for the Preparation of Technetium Tc99m Sulfur Colloid Injection for Subcutaneous, Intraperitoneal, Intravenous, and Oral Use", Pharmalucence Inc., Reference ID: 2977567, Prescribing Information, 10 P., Jul. 2011.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Official Action Dated May 23, 2011 From the US Patent and Trademark Office Re. U.S. Appl. No. 11/667,793.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Chengazi et al. "Imaging Prostate Cancer With Technetium-99m-7E11-C5.3 (CYT-351)", Journal of Nuclear Medicine, 38: 675-682, 1997.
McJilton et al. "Protein Kinase Cε Interacts With Bax and Promotes Survival of Human Prostate Cancer Cells", Oncogene, 22; 7958-7968, 2003.
Xu et al. "Quantitative Expression Profile of Androgen-Regulated Genes in Prostate Cancer Cells and Identification of Prostate-Specific Genes", International Journal of Cancer, 92: 322-328, 2001.
Communication Pursuant to Article 94(3) EPC Dated May 29, 2012 From the European Patent Office Re. Application No. 05803689.8.
Communication Under Rule 71(3) EPC Dated May 30, 2012 From the European Patent Office Re.: Application No. 02716285.8.
Interview Summary Dated May 31, 2011 From the US Patent and Trademark Office Re. U.S. Appl. No. 10/616,301.
Communication Pursuant to Article 94(3) EPC Dated Jun. 11, 2012 From the European Patent Office Re.: Application No. 06756259.5.
Dillman "Radiolabeled Anti-CD20 Monoclonal Antibodies for the Treatment of B-Cell Lymphoma", Journal of Clinical Oncology, 20(16): 3545-3557, Aug. 15, 2002.
Sands et al. "Methods for the Study of the Metabolism of Radiolabeled Monoclonal Antibodies by Liver and Tumor", The Journal of Nuclear Medicine, 28: 390-398, 1987.
Official Action Dated Jun. 21, 2012 From the US Patent and Trademark Office Re. U.S. Appl. No. 12/309,479.
Notice of Allowance Dated Jun. 23, 2011 From the US Patent and Trademark Office Re.: U.S. Appl. No. 10/616,301.
Advisory Action Before the Filing of an Appeal Brief Dated Jul. 12, 2012 From the US Patent and Trademark Office Re. U.S. Appl. No. 11/667,793.
Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Apr. 23, 2012 From the US Patent and Trademark Office Re. U.S. Appl. No. 11/932,987.
Official Action Dated Jun. 28, 2011 From the US Patent and Trademark Office Re. U.S. Appl. No. 11/628,074.
Examination Report Dated Jun. 22, 2011 From the Government of India, Patent Office, Intellectual Property Building Re. Application No. 2963/CHENP/2006.
Official Action Dated Mar. 9, 2011 From the US Patent and Trademark Office Re.: U.S. Appl. No. 10/616,301.
Response Dated Jun. 7, 2011 to Official Action of Mar. 9, 2011 From the US Patent and Trademark Office Re.: U.S. Appl. No. 10/616,301.
Response Dated Jun. 28, 2011 to Official Action of Dec. 28, 2010 From the US Patent and Trademark Office Re.: U.S. Appl. No. 11/607,075.
Official Action Dated Jul. 11, 2011 From the US Patent and Trademark Office Re.: U.S. Appl. No. 11/980,683.
Response Dated Jul. 14, 2011 to Official Action of Mar. 15, 2011 From the US Patent and Trademark Office Re.: U.S. Appl. No. 10/343,792.
Official Action Dated Jul. 12, 2011 From the US Patent and Trademark Office Re.: U.S. Appl. No. 09/641,973.
Official Action Dated Jul. 30, 2012 From the US Patent and Trademark Office Re.: U.S. Appl. No. 11/980,683.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Official Action Dated Aug. 2, 2012 From the US Patent and Trademark Office Re. U.S. Appl. No. 12/087,150.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Response Dated Sep. 1, 2011 to Communication Pursuant to Article 94(3) EPC of Mar. 2, 2011 From the European Patent Office Re.: Application No. 06756259.5.
Response Dated Aug. 29, 2011 to Official Action of Apr. 27, 2011 From the US Patent and Trademark Office Re.: U.S. Appl. No. 10/836,223.
Official Action Dated Aug. 31, 2012 From the US Patent and Trademark Office Re. U.S. Appl. No. 11/980,653.
Official Action Dated Sep. 12, 2011 From the US Patent and Trademark Office Re. U.S. Appl. No. 11/980,653.
Official Action Dated Sep. 12, 2011 From the US Patent and Trademark Office Re. U.S. Appl. No. 12/087,150.
Response Dated Sep. 12, 2011 to Official Action of Jul. 11, 2011 From the US Patent and Trademark Office Re.: U.S. Appl. No. 11/980,683.
Response Dated Sep. 20, 2011 to Official Action of Apr. 20, 2011 From the US Patent and Trademark Office Re.: U.S. Appl. No. 11/798,017.
Communication Pursuant to Article 94(3) EPC Dated Sep. 22, 2011 From the European Patent Office Re. Application No. 06756258.7.

(56) References Cited

OTHER PUBLICATIONS

Notice of Allowance Dated Sep. 16, 2011 From the US Patent and Trademark Office Re.: U.S. Appl. No. 11/607,075.
Official Action Dated Sep. 13, 2011 From the US Patent and Trademark Office Re. U.S. Appl. No. 11/976,852.
Ellestad "Stress Testing: Principles and Practice", XP008143015, 5th Edition, p. 432, Jan. 1, 2003.
Gilland et al. "Long Focal Length, Asymmetric Fan Beam Collimation for Transmission Acquisition With a Triple Camera SPECT System", IEEE Transactions on Nuclear Science, XP011087666, 44(3): 1191-1196, Jun. 1, 1997.
Meyers et al. "Age, Perfusion Test Results and Dipyridamole Reaction", Radiologic Technology, XP008142909, 73(5): 409-414, May 1, 2002.
Zhang et al. "Potential of a Compton Camera for High Performance Scintimammography", Physics in Medicine and Biology, XP020024019, 49(4): 617-638, Feb. 21, 2004.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Notice of Allowance Dated Sep. 28, 2012 From the US Patent and Trademark Office Re. U.S. Appl. No. 12/792,856.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.
Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanki "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Response Dated Oct. 14, 2011 to Supplementary European Search Report and the European Search Opinion of Mar. 16, 2011 From the European Patent Office Re. Application No. 05803689.8.
Official Action Dated Oct. 11, 2012 From the US Patent and Trademark Office Re. U.S. Appl. No. 11/976,852.
Official Action Dated Oct. 26, 2011 From the US Patent and Trademark Office Re.: U.S. Appl. No. 10/836,223.
Official Action Dated Oct. 27, 2011 From the US Patent and Trademark Office Re.: U.S. Appl. No. 11/656,548.
Supplemental Notice of Allowability Dated Oct. 24, 2011 From the US Patent and Trademark Office Re.: U.S. Appl. No. 11/607,075.
Official Action Dated Oct. 10, 2012 From the US Patent and Trademark Office Re. U.S. Appl. No. 11/798,017.
Communication Pursuant to Article 94(3) EPC Dated Oct. 26, 2012 From the European Patent Office Re. Application No. 05803689.8.
Notice of Allowance Dated Oct. 11, 2011 From the US Patent and Trademark Office Re. U.S. Appl. No. 11/988,926.
Response Dated Oct. 14, 2011 to Communication Pursuant to Rules 70(2) and 70a(2) EPC of Apr. 4, 2011 From the European Patent Office Re. Application No. 05803689.8.

Restriction Official Action Dated Nov. 8, 2011 From the US Patent and Trademark Office Re. U.S. Appl. No. 12/309,479.
Communication Pursuant to Article 94(3) EPC Dated Nov. 12, 2012 From the European Patent Office Re. Application No. 06756258.7.
Notice of Allowance Dated Nov. 15, 2012 From the US Patent and Trademark Office Re.: U.S. Appl. No. 11/980,683.
Response Dated Nov. 14, 2011 to Official Action of Sep. 12, 2011 From the US Patent and Trademark Office Re. U.S. Appl. No. 12/087,150.
Response Dated Oct. 24, 2011 to Official Action of May 23, 2011 From the US Patent and Trademark Office Re. U.S. Appl. No. 11/667,793.
Restriction Official Action Dated Nov. 15, 2011 From the US Patent and Trademark Office Re. U.S. Appl. No. 11/980,683.
Summons to Attend Oral Proceedings Pursuant to Rule 115(1) EPC Dated Nov. 29, 2012 From the European Patent Office Re. Application No. 06756259.5.
Communication Pursuant to Article 94(3) EPC Dated Nov. 18, 2011 From the European Patent Office Re. Application No. 05803689.8.
Response Dated Nov. 14, 2011 to Official Action of Jul. 12, 2011 From the US Patent and Trademark Office Re.: U.S. Appl. No. 09/641,973.
Response Dated Nov. 23, 2011 to Official Action of May 23, 2011 From the US Patent and Trademark Office Re.: U.S. Appl. No. 10/616,307.
Response Dated Nov. 23, 2011 to Official Action of May 23, 2011 From the US Patent and Trademark Office Re.: U.S. Appl. No. 11/980,690.
Response Dated Nov. 28, 2011 to Official Action of Jun. 28, 2011 From the US Patent and Trademark Office Re. U.S. Appl. No. 11/628,074.
Official Action Dated Nov. 1, 2010 From the US Patent and Trademark Office Re.: U.S. Appl. No. 11/980,690.
Pluim et al. "Image Registration by Maximization of Combined Mutual Information and Gradient Information", IEEE Transactions on Medical Imaging, 19(8): 1-6, 2000.
Response Dated Dec. 8, 2011 to Restriction Official Action of Nov. 8, 2011 From the US Patent and Trademark Office Re. U.S. Appl. No. 12/309,479.
Official Action Dated Mar. 11, 2013 From the US Patent and Trademark Office Re. U.S. Appl. No. 13/345,719.
Official Action Dated Jun. 12, 2013 From the US Patent and Trademark Office Re. U.S. Appl. No. 12/087,150.
Bacharach et al. "Attenuation Correction in Cardiac Positron Emission Tomography and Single-Photon Emission Computed Tomography", Journal of Nucelar Cardiology, 2(3): 246-255, 1995.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.
Notice of Allowance Dated Jun. 14, 2013 From the US Patent and Trademark Office Re. U.S. Appl. No. 10/616,307.
Notice of Allowance Dated Jul. 19, 2013 From the US Patent and Trademark Office Re. U.S. Appl. No. 11/989,223.
Notice of Allowance Dated Jul. 25, 2013 From the US Patent and Trademark Office Re. U.S. Appl. No. 13/345,719.
Supplementary European Search Report and the European Search Opinion Dated Nov. 13, 2012 From the European Patent Office Re. Application No. 06728347.3.
Notice of Allowance Dated Mar. 14, 2013 From the US Patent and Trademark Office Re.: U.S. Appl. No. 11/798,017.
Studen "Compton Camera With Position-Sensitive Silicon Detectors", Doctoral Thesis, University of Ljubljana, Faculty of Mathematics and Physics, 36 P.
Notice of Allowance Dated Apr. 10, 2013 From the US Patent and Trademark Office Re. U.S. Appl. No. 11/976,852.
Applicant-Initiated Interview Summary Dated May 1, 2013 From the US Patent and Trademark Office Re. U.S. Appl. No. 10/343,792.
Applicant-Initiated Interview Summary Dated May 1, 2013 From the US Patent and Trademark Office Re. U.S. Appl. No. 11/980,653.
Notice of Allowance Dated Jun. 21, 2013 From the US Patent and Trademark Office Re. U.S. Appl. No. 11/980,653.

(56) References Cited

OTHER PUBLICATIONS

Advisory Action before the Filing of an Appeal Brief Dated May 21, 2013 From the US Patent and Trademark Office Re. U.S. Appl. No. 11/980,653.
Notice of Allowance Dated Jul. 15, 2013 From the US Patent and Trademark Office Re. U.S. Appl. No. 11/932,987.
Official Action Dated Jul. 5, 2013 From the US Patent and Trademark Office Re.: U.S. Appl. No. 11/656,548.
Advisory Action Before the Filing of an Appeal Brief Dated Feb. 26, 2013 From the US Patent and Trademark Office Re. U.S. Appl. No. 11/989,223.
Official Action Dated Nov. 30, 2012 From the US Patent and Trademark Office Re. U.S. Appl. No. 11/989,223.
Notice of Allowance Dated Oct. 26, 2012 From the US Patent and Trademark Office Re. U.S. Appl. No. 12/514,785.
Official Action Dated Nov. 30, 2012 From the US Patent and Trademark Office Re. U.S. Appl. No. 12/514,785.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tomai et al. "A 3D Gantry Single Photon Emission Tomograph With Hemispherical Coverage for Dedicated Breast Imaging", Nuclear Instruments & Methods in Physics Research, Section A, 497: 157-167, 2003.
Advisory Action Before the Filing of an Appeal Brief Dated Feb. 26, 2013 From the US Patent and Trademark Office Re. U.S. Appl. No. 12/514,785.
Notice of Allowance Dated Feb. 21, 2013 From the US Patent and Trademark Office Re. U.S. Appl. No. 11/798,017.
Notice of Allowance Dated Feb. 25, 2013 From the US Patent and Trademark Office Re.: U.S. Appl. No. 09/641,973.
Communication Under Rule 71(3) EPC Dated Feb. 26, 2013 From the European Patent Office Re. Application No. 06756259.5.
Official Action Dated Feb. 22, 2013 From the US Patent and Trademark Office Re.: U.S. Appl. No. 10/616,307.
Notice of Allowance Dated Mar. 7, 2013 From the US Patent and Trademark Office Re. U.S. Appl. No. 13/726,316.
Applicant-Initiated Interview Summary Dated Jan. 28, 2013 From the US Patent and Trademark Office Re.: U.S. Appl. No. 11/798,017.
Official Action Dated Feb. 7, 2013 From the US Patent and Trademark Office Re. U.S. Appl. No. 11/980,653.
Notice of Allowance Dated Dec. 26, 2012 From the US Patent and Trademark Office Re.: U.S. Appl. No. 11/980,690.
Official Action Dated Dec. 28, 2012 From the US Patent and Trademark Office Re.: U.S. Appl. No. 10/343,792.
Charland et al. "The Use of Deconvolution and Total Least Squares in Recovering a Radiation Detector Line Spread Function", Medical Physics, 25(2): 152-160, Feb. 1998. Abstract Only!
Applicant-Initiated Interview Summary Dated Jan. 29, 2014 From the US Patent and Trademark Office Re. U.S. Appl. No. 13/345,773.
Communication Pursuant to Article 94(3) EPC Dated Nov. 25, 2013 From the European Patent Office Re. Application No. 06756258.7.
Notice of Allowance Dated Dec. 17, 2013 From the US Patent and Trademark Office Re. U.S. Appl. No. 13/913,804.
Official Action Dated Nov. 15, 2013 From the US Patent and Trademark Office Re. U.S. Appl. No. 13/345,773.
Official Action Dated Dec. 16, 2013 From the US Patent and Trademark Office Re. U.S. Appl. No. 12/087,150.
Communication Pursuant to Article 94(3) EPC Dated Sep. 16, 2013 From the European Patent Office Re.: Application No. 06832278.3.
Notice of Allowance Dated Aug. 20, 2013 From the US Patent and Trademark Office Re. U.S. Appl. No. 11/932,872.
Official Action Dated Aug. 5, 2013 From the US Patent and Trademark Office Re. U.S. Appl. No. 12/309,479.
Official Action Dated Sep. 5, 2013 From the US Patent and Trademark Office Re. U.S. Appl. No. 13/947,198.
Supplemental Notice of Allowability Dated Aug. 20, 2013 From the US Patent and Trademark Office Re. U.S. Appl. No. 11/980,653.
Berman et al. "D-SPECT: A Novel Camera for High Speed Quantitative Molecular Imaging: Initial Clinical Results", The Journal of Nuclear Medicine, 47(Suppl. 1): 131P, 2006.
Berman et al. "Myocardial Perfusion Imaging With Technetium-99m-Sestamibi: Comparative Analysis of Available Imaging Protocols", The Journal of Nuclear Medicine, 35: 681-688, 1994.
Borges-Neto et al. "Perfusion and Function at Rest and Treadmill Exercise Using Technecium-99m-Sestamibi: Comparison of One- and Two-Day Protocols in Normal Volunteers", The Journal of Nuclear Medicine, 31(7): 1128-1132, Jul. 1990.
Kwok et al. "Feasability of Simultaneous Dual-Isotope Myocardial Perfusion Acquisition Using a Lower Dose of Sestamibi", European Journal of Nuclear Medicine, 24(3): 281-285, Mar. 1997.
Patton et al. "D-SPECT: A New Solid State Camera for High Speed Molecular Imaging", The Journal of Nuclear Medicine, 47(Suppl. 1): 189P, 2006.
Official Action Dated Apr. 11, 2014 From the US Patent and Trademark Office Re. U.S. Appl. No. 12/309,479.
Sharir et al. "D-SPECT: High Speed Myocardial Perfusion Imaging: A Comparison With Dual Detector Anger Camera (A-SPECT)", The Journal of Nuclear Medicine, 48(Suppl. 2): 51P, # 169, 2007.
Applicant-Initiated Interview Summary Dated Mar. 20, 2014 From the US Patent and Trademark Office Re. U.S. Appl. No. 12/087,150.
Official Action Dated Feb. 10, 2014 From the US Patent and Trademark Office Re. U.S. Appl. No. 11/667,793.
Official Action Dated Jul. 30, 2013 From the US Patent and Trademark Office Re. U.S. Appl. No. 10/343,792.
Official Action Dated Jul. 31, 2013 From the US Patent and Trademark Office Re. U.S. Appl. No. 11/667,793.
Communication Pursuant to Article 94(3) EPC Dated May 8, 2014 From the European Patent Office Re. Application No. 05803689.8.
Communication Pursuant to Article 94(3) EPC Dated Oct. 10, 2014 From the European Patent Office Re. Application No. 05803689.8.
Communication Pursuant to Article 94(3) EPC Dated Oct. 17, 2014 From the European Patent Office Re. Application No. 06809851.6.
Communication Pursuant to Article 94(3) EPC Dated Sep. 12, 2014 From the European Patent Office Re. Application No. 06832278.3.
Official Action Dated Jun. 17, 2014 From the US Patent and Trademark Office Re. U.S. Appl. No. 12/087,150.
Official Action Dated Jul. 8. 2015 From the US Patent and Trademark Office Re. U.S. Appl. No. 11/667,793.
Applicant-Initiated Interview Summary Dated Jun. 11, 2015 From the US Patent and Trademark Office Re. U.S. Appl. No. 14/214,960.
Official Action Dated Apr. 15, 2015 From the US Patent and Trademark Office Re. U.S. Appl. No. 14/214,960.
Official Action Dated Mar. 26, 2015 From the US Patent and Trademark Office Re. Application No. 14/147,682.
Official Action Dated Dec. 4, 2014 From the US Patent and Trademark Office Re. U.S. Appl. No. 12/087,150.
Johnson et al. "Analysis and Reconstruction of Medical Images Using Prior Information", Lectures Notes in Statistics, Case Studies in Bayesian Statistics, II: 149-228, 1995.
Official Action Dated Aug. 4, 2015 From the US Patent and Trademark Office Re. U.S. Appl. No. 14/082,314.
Official Action Dated Sep. 15, 2015 From the US Patent and Trademark Office Re. U.S. Appl. No. 14/147,682.

\* cited by examiner

METHOD, A SYSTEM, AND AN APPARATUS FOR USING AND PROCESSING MULTIDIMENSIONAL DATA

RELATED APPLLICATIONS

The application is a National Phase Application of PCT Patent Application No. PCT/IL2007/001588 having International Filing Date of Dec. 20, 2007, which claims priority from U.S. Provisional Application No. 60/875,833, filed on Dec. 20, 2006. The contents of the above Application are all incorporated herein by reference.

FIELD AND BACKGROUND OF THE INVENTION

The present invention, in some embodiments thereof, relates to a system and a method for analyzing a multidimensional patient profile and, more particularly, but not exclusively, to a system and a method for analyzing a multidimensional patient profile that includes a medical image.

Systems and devices for visualizing the inside of living organisms are among the most important medical developments in the last thirty years. Systems like computerized tomography (CT), magnetic resonance imaging (MRI), a positron emission tomography (PET), and a single photon emission computed tomography (SPECT) scanners allow physicians to examine internal tissues or areas of the body that require a thorough examination. In use, the visualizing scanner outputs a 3D medical image, such as a sequence of computerized cross-sectional images of one or more tissues, which is then interpreted by specialized radiologists.

It should be noted that other imaging devices and methods are also known, for example as disclosed in International patent application Pub. No. WO2006/051531, which has been published on May 18, 2006 and incorporated herein by reference. This patent application describes an apparatus for radiation based imaging of a non-homogenous target area having distinguishable regions therein. The apparatus comprises an imaging unit designed to obtain radiation intensity data from the target region in the spatial dimensions and one or more other dimensions. The apparatus further comprises an image four-dimension analysis unit associated with the imaging unit for analyzing said obtained intensity data in the spatial dimension, and the one or more other dimensions, in order to map the distinguishable regions.

Commonly, a patient is referred for a visual scan by a general practitioner or an expert practitioner. The 3D medical image is forwarded to and diagnosed by a general radiologist who is responsible for the analysis and diagnosis of the medical image. The medical images and the diagnosis thereof are sent back to the referring practitioner.

In most hospitals and radiology centers, the 3D medical images are transferred to a picture archiving communication system (PACS) before being accessed by the radiologists. The PACS is installed on one or more of computers, which are dedicated for storing, retrieving, distributing and presenting the stored 3D medical images. The 3D medical images are stored in an independent format. The most common format for image storage is digital imaging and communications in medicine (DICOM).

Typically, a PACS network consists of a central server that stores a database containing the images connected to one or more clients via a local area network (LAN) or a wide area network (WAN) which provide or utilize the images. Web-based PACS is becoming more and more common: these systems utilize the Internet as their means of communication, usually via a virtual private network (VPN) or a secure sockets layer (SSL). The software in thin or smart client is loaded via ActiveX, Java, or .NET Framework. Definitions vary, but most claim that for a system to be truly web based, each individual image should have its own URL. Client workstations can use local peripherals for scanning image films into the system, printing image films from the system and interactive display of digital images. Modern radiology equipment, modalities, feed patient images directly to the PACS in digital form. For backwards compatibility, most hospital imaging departments and radiology practices employ a film digitizer.

Computer aided detection (CAD) systems that assist physicians in diagnosing pathological, traumatic, or healthy indications are known. However, these CAD system are usually based on fixed expert rules and a closed list of treatments. For example, U.S. Pat. No. 6,188,988 and U.S. Pat. No. 6,081,786, which have been granted on Feb. 13, 2001, disclose systems, methods and computer program products for guiding selection of a therapeutic treatment regimen for a known disease such as HIV infection, are disclosed. The method comprises providing patient information to a computing device (the computer device comprising: a first knowledge base comprising a plurality of different therapeutic treatment regimens for the disease; a second knowledge base comprising a plurality of expert rules for selecting a therapeutic treatment regimen for the disease; and a third knowledge base comprising advisory information useful for the treatment of a patient with different constituents of the different therapeutic treatment regimens; and generating in the computing device a listing (preferably a ranked listing) of therapeutic treatment regimens for the patient; and generating in the computing device advisory information for one or more treatment regimens in the listing based on the patient information and the expert rules.

SUMMARY OF THE INVENTION

According to one aspect of the present invention there is provided a method for analyzing a functional map of at least one tissue of a patient. The method comprises managing a plurality of functional maps each being associated with a plurality of first biological activity indications, receiving a functional map being associated with a plurality of second biological activity indications, identifying a matching set of the managed functional maps by matching between the plurality of first and second biological activity indications, and using the matching set for a member of a group consisting of: an image data acquisition, a diagnosis of the received functional map, a classification of the received functional map. Optionally, the received functional map is associated with first medical information related to the current patient, each the managed functional map being associated with second medical information, the matching comprises matching between the first and second medical information.

Optionally, the received and managed functional maps are pixelated.

More optionally, at least some pixel elements of the received pixelated functional map is associated with the plurality of first biological activity indications, at least some pixel elements of each the pixelated functional map is associated with the plurality of second biological activity indications, the matching being between respective pixel elements of the received and managed pixelated functional map.

Optionally, the method comprises preprocessing the received functional map before the matching; the preprocessing comprises a member of a group consisting of: registering the received functional map according to at least one of the functional maps and denoising the received functional map.

More optionally, each the first and second medical information comprises a member of a group consisting of: a laboratory result, a therapeutic procedure record, a clinical evaluation, an age, a gender, a medical condition, identification information, genetic information, a patient medical record, a metabolism data, blood pressure, a sensitivity, an allergy, a population relevance, an epidemiologic classification, a patient history, and a treatment method.

Optionally, each the received and managed functional map comprises a member of a group consisting of: a positron emission tomography (PET), a PET—computerized tomography (CT), a single photon emission computed tomography (SPECT), an extracorporeal gamma scan, an extracorporeal beta scan, an intracorporeal gamma scan, and an intracorporeal beta scan.

Optionally, each the first and second plurality of biological activity indications comprises an uptake level of radiation emitted from a plurality of tracers.

Optionally, managing the plurality of functional maps comprises at least one prototype of a pathological biological activity.

Optionally, at least one of the managed functional map is associated a pathological diagnosis, the diagnosis of the received functional map being determined according to the pathological diagnosis of members of the matching set.

Optionally, the managing comprises managing more than 1,000,000 functional maps.

Optionally, the matching comprises matching topological similarities between the received functional map and at least one of the plurality of managed functional maps.

Optionally, the matching comprises matching common radiation emission pattern between the received functional map and at least one of the plurality of managed functional maps.

Optionally, the received functional map and at least one of the plurality of managed functional maps are kinetic functional maps.

Optionally, at least one of the plurality of managed functional maps is associated with a method of treatment and with a success evaluation thereof, the using comprises outputting a treatment recommendation according to respective the evaluation of at least one member of the matching set.

Optionally, the method further identify a plurality of biological pathways in the received and managed functional maps respectively according to the first and second plurality of biological activity indications, the matching comprises matching the plurality of biological pathways.

Optionally, the using comprises classifying the functional map.

Optionally, the using is performed in real time.

According to one aspect of the present invention there is provided a system for analyzing a functional map of at least one tissue of a current patient. The system comprises an input unit configured for receiving the functional map being associated with a plurality of first biological activity indications and a database configured for storing a plurality of functional maps, each being associated with a plurality of second biological activity indications. The system further comprises an analyzing unit for identifying a matching set of the stored functional maps by matching between the plurality of first and second biological activity indications. The matching set is used for a member of a group consisting of: an image data acquisition and treatment.

Optionally, the system further comprises an integration module configured for preprocessing the functional map, the preprocessing comprises a member of a group comprises: registering the functional map according to at least one of the stored plurality of functional maps and converting the functional map to a data format of at least one of the stored plurality of functional maps.

Optionally, the system further comprises a display unit configured for displaying the matching set.

Optionally, the analyzing unit is configured for weighing member of the matching set according to their potential relevance to the received functional map.

According to one aspect of the present invention there is provided a distributed system for analyzing a functional map of at least one tissue of a current patient. The system comprises a plurality of client terminals each configured for receiving the functional map being associated with a plurality of first biological activity indications, a database configured for storing a plurality of functional maps, each being associated with a plurality of second biological activity indications, and an analyzing unit for matching between the plurality of first and second biological activity indications. The matching is used for a member of a group consisting of: an image data acquisition, a diagnosis of the received functional map, a classification of the received functional map.

According to one aspect of the present invention there is provided a research tool for identifying a trial group. The research tool comprises an input unit configured for receiving a set of characteristics defining a patient profile, a database configured for storing a plurality patient profiles, an analyzing unit for identifying a trial group by matching between the set of characteristics and the plurality patient profiles, and an output unit for outputting the trial group.

Optionally, each the patient profile being associated with a functional image.

Optionally, the trial group is a control group.

Optionally, the set of characteristics comprises at least one first biological activity, at least one of the plurality patient profiles comprises at least one second biological activity analyzing unit for identifying a trial group by matching between the at least one first biological activity and the at least one second biological activity.

According to one aspect of the present invention there is provided an imaging system for capturing a functional image of at least one tissue of a patient. The imaging system comprises at least one detector for obtaining a source functional image being associated with at least one first biological activity indication, a database configured for storing a plurality of reference functional images each being associated with at least one second biological activity indication, and an analyzing unit for matching between the at least one first and second biological activity indications. The analyzing unit is configured for controlling the at least one detector according to the matching.

Optionally, the functional image depicts a segment of a requested area, the controlling comprises maneuvering the at least one detector to capture an additional segment of the requested area according to the matching.

Optionally, the detector comprises a radiation transmitting unit for emitting radiation toward the segment; the controlling comprises adjusting the intensity of the emitted radiation according to the matching.

Optionally, the detector is configured for obtaining the functional image, by a first modality, selected from the group consisting of a single photon emission computed tomography (SPECT) unit, a positron emission tomography (PET) unit, an extracorporeal, hand-held gamma scan unit, an extracorporeal unit, hand-held beta scan, an intracorporeal gamma scan, an intracorporeal beta scan, an intravascular gamma scan, and an intravascular beta scan.

Optionally, the source functional image is a preliminary image mapping a radiation emitted from a first tracer; the controlling comprises outputting a recommendation for the injection of a second tracer based on the matching.

According to one aspect of the present invention there is provided a method for obtaining a functional image of at least one tissue of a patient. The method comprises a) receiving a preliminary functional image associated with at least one first biological activity indication, b) matching between the at least one first biological activity and a plurality of respective biological activities each of a reference functional image, and c) outputting a instructions for obtaining an additional preliminary functional image according to the matching.

Optionally, the method further comprises d) obtaining the additional preliminary functional image according to the instructions and e) combining the preliminary functional images producing a final functional image.

Optionally, the method further comprises repeating b)-e), the at least one first biological activity are taken from the final functional image.

Optionally, the instructions comprises a member of a group comprises: an identifier defining which tracer to use during the obtaining, an identifier defining in which concentration to use a tracer during the obtaining, a point of view of at least one detector which is used for the obtaining, a region of interest to be imaged during the obtaining, and refining the preliminary functional image.

According to one aspect of the present invention there is provided a method for calculating a treatment recommendation. The method comprises a) managing a plurality of patient profiles each being associated with a plurality of patient medical records, at least one treatment, and an outcome evaluation of the at least one treatment, b) receiving a current patient profile being associated with a plurality of related medical records, c) identifying a matching set of the managed patient profiles by matching between the plurality of patient and related medical records, and d) calculating a medical recommendation according to the at least one treatment of members of the matching set.

Optionally, the plurality of patient profiles includes the at least 1,000,000 patient profiles.

Optionally, each the patient profile having a functional map, each the functional map being associated with a plurality of biological activity indications, the identifying comprises identifying the matching set by matching between biological activity indications of the current patient profile and the plurality of patient profiles.

Optionally, each the plurality of patient medical records comprises a member of a group consisting of: a laboratory result, a therapeutic procedure record, a clinical evaluation, an age, a gender, a medical condition, identification information, genetic information, a patient medical record, a metabolism data, blood pressure, a sensitivity, an allergy, a population relevance, an epidemiologic classification, a patient history, and a treatment method.

Optionally, at least some of the plurality of patient medical records are associated with a time tag indicating a related occurrence or examination time.

Optionally, each the at least one treatment is associated with a reliability score, the calculating comprises calculating the medical recommendation according to the reliability score of members of the matching set.

Optionally, each the patient profile is associated with a current treatment record, the identifying comprises identifying the matching set by matching between current treatment records of the current patient profile and of the plurality of patient profiles, and the medical recommendation comprises a continuation treatment for the current patient profile.

More optionally, the current treatment record profile is associated with a respective outcome evaluation.

Optionally, the method further comprises e) updating the current treatment record of the current patient profile with the medical recommendation and the respective outcome evaluation with an outcome of a respective treatment and f) repeating a)-d) the current treatment record is the updated current patient profile and the respective outcome evaluation is the outcome of a respective treatment.

Optionally, the medical recommendation is a medical recommendation of a phase in an ongoing treatment and the outcome is a current outcome of the phase, the updating and repeating are performed during the ongoing treatment.

Optionally, the medical recommendation comprises a request for an additional evolution. The method further comprises e) updating at least one of the plurality of patient medical records with the additional evolution and f) repeating a)-d) the current patient profile being updated with the additional evolution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data.

Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
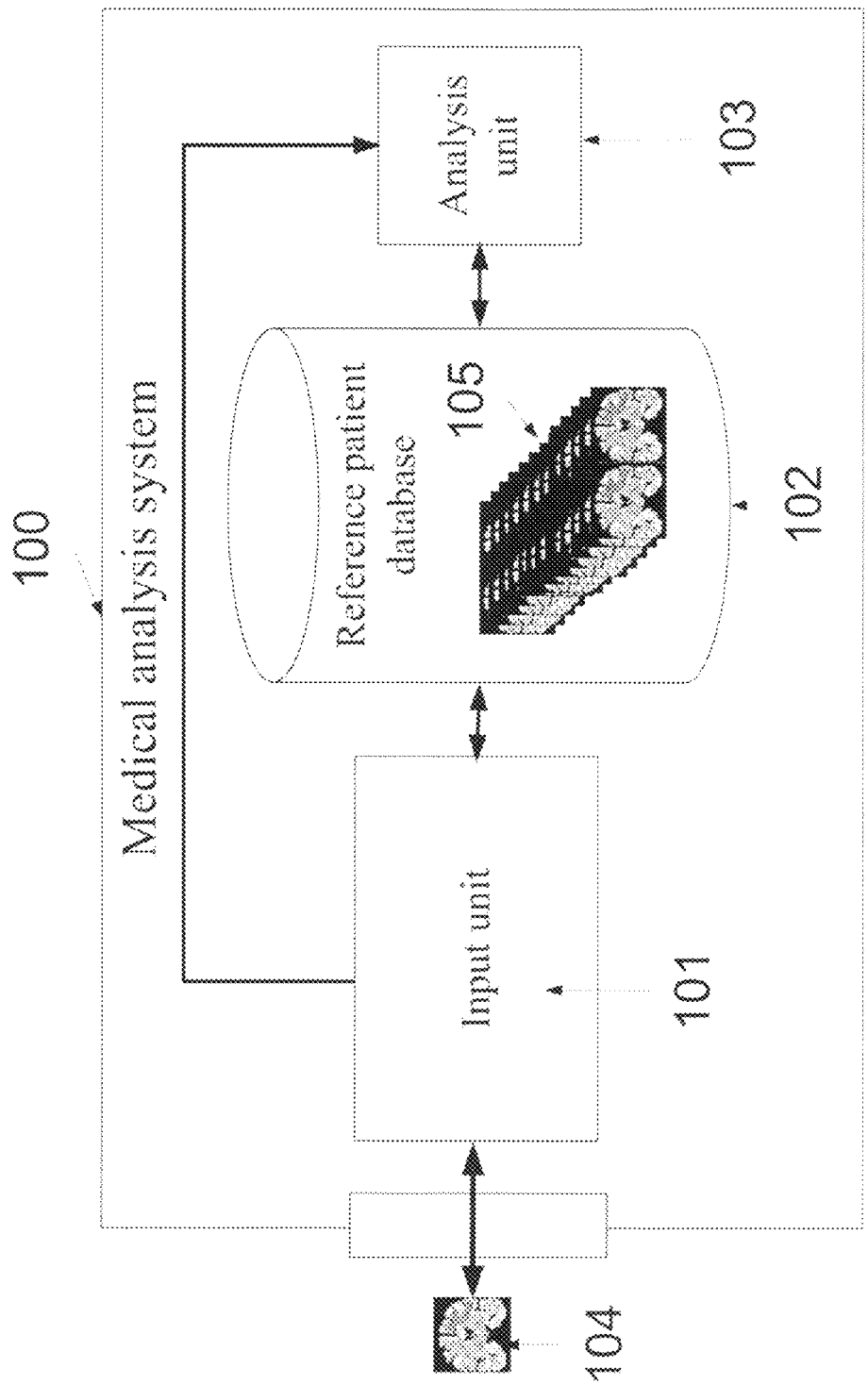
FIG. 1 is a schematic illustration of a matching system for analyzing a functional map of one or more tissues of a patient, according to an exemplary embodiment of the present invention.

Exemplary embodiments of the present invention describe methods and systems for calculating a treatment recommendation. These embodiments are based on a plurality of reference patient profiles; each includes a plurality of patient medical records, at least one given treatment, and an outcome evaluation of the given treatment. A current patient profile, which is associated with a plurality of related medical records, is received and matched with the reference patient profiles. The match allows the identification of a matching set that includes members with patient medical records that have a certain potential relevance to the patient medical records of the current patient profile. Each record of the matching set specifies a certain given treatment and the outcome thereof The matching set allows the calculation of a medical recommendation according to given the treatments which are specified in the matching set. For example, the medical recommendation may be based on the identification of a treatment that has a positive outcome evaluation, the most prevalent positive outcome evaluation, or a combination of the level of success of the possible outcome evaluations and/or the prevalence of the possible outcome evaluations.

Exemplary embodiments of the present invention describe methods and systems for analyzing, optionally in real time, patient data, such as a functional map, functional image, such as PET and SPECT images, and/or patient profile, of a patient using a reference database that contain a plurality of reference functional images, functional maps, and/or patient profiles. These embodiments allow, inter alia, identifying a matching set of functional images, maps, and/or patient profiles from the reference database by matching between the patient data and records of a reference database. Such a matching set can be used for identifying, classifying, and/or diagnosing pathological indications, which are depicted in the functional image, and for alarming and/or notifying the physician about such pathological indications.

Optionally, the matching set is used for refining the process of acquiring the functional image.

Optionally, the reference database is used for managing a plurality of patient profiles. Each patient profile comprises one or more functional images, each as defined above and medical information that is related to the patients which are imaged in the one or more of the functional images.

Optionally, the system is used for locally refining the received functional image. The received functional image may depict a segment of a certain requested area, a preliminary image that depicts partial emissions of one or more tracers, and/or an incomplete imaging of a certain area. In such an embodiment, each matching set may be used for generating instructions to an imaging system, thereby allowing an active vision, optionally as described below.

Optionally, this refinement allows reducing the number of detectors which are needed for capturing the functional image, reducing the computational complexity which is needed for reconstructing the received functional image and/ or for reducing the amount and/or medicaments concentration which are injected to the patient. Exemplary embodiments of the present invention are a research tool generates trials groups, such as control groups, for experiments, using a using a reference database that comprises a plurality of functional images and/or patient profiles.

Some exemplary embodiments of the present invention describe a method that includes managing a plurality of pixelated functional maps, each map or a pixel element thereof is associated with a plurality of biological activity indications, such as values that represent the emission of one or more tracers, for example radionuclide sodium-24 tracers, from one or more tissues. When a pixelated functional map of a patient that is associated with a plurality of such biological activity indications is received, the managing allows the identification of a matching set that includes functional images that record respective biological activity indications. The matching set is used for image data acquisition, diagnosing the received functional map, refining the received functional map, operating the imaging system that created the functional image, and/or for classifying the received functional map.

Optionally, as a high computational complexity may be needed in order to match between the new functional map and the stored functional maps, a hardware architecture that allows heavy processing may be used, optionally as described below. Such architecture can be used to reduce the processing time of the matching and/or analysis process.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Reference is now made to FIG. 1, which is a schematic illustration of a matching system 100 for analyzing a functional map or a functional image, of one or more tissues of a patient, according to an exemplary embodiment of the present invention. The matching system 100 comprises an input unit 101 for obtaining one or more functional images 104 of one or more tissues of a patient. For brevity, a received functional image, which is an output of an imaging system that depicts one or more tissues of a patient and/or a received functional map, which is a set of data that describes and/or defines biological and/or pathological indications in one or more tissues of a patient, are referred to as a source image 104. The system further comprises a reference patient database 102 for managing a plurality of functional images 105. As used herein, managing a plurality of functional images means hosting, searching, manipulating, and/or accessing a plurality of functional images. For brevity, the hosted functional images and/or the functional maps are referred to in this application as reference images 105. The matching system 100 further comprises an analysis unit 103 for matching between the source image 104 and the reference images 105.

In some embedment of the present invention, the matching system 100 is used as a CAD system that assist physicians, such as radiologists, in diagnosing pathological, traumatic, or healthy indications in the source image 104. The matching system 100 assists physicians by leveraging the reference images 105 and additional dimensions which are associated therewith, optionally as described below, to identify relevant medical cases and their courses/acquisition, methods, treatments, and the like. In such an embodiment, the matching system 100 may assist physicians to identify cancerous, juxta cancerous, wounded, and normal tissues.

Optionally, the matching system 100 is used for automatic diagnosis of the patient. Optionally, the matching system 100 is used for alerting a patient, a physician, and/or a central server that is used for monitoring patients about a certain biological activity and/or inactivity in the patient body. The system may also be used as a research tool that allows a researcher to define a control group or a test group, as further described below.

Figure 2:
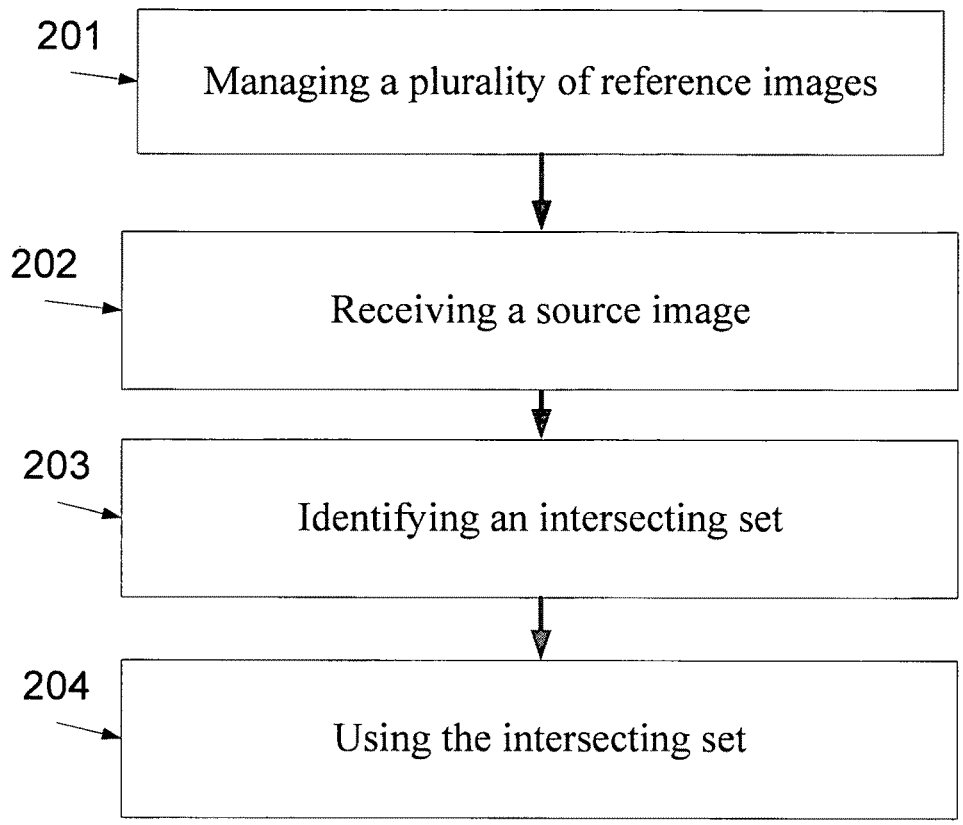
FIG. 2 is a flowchart of a method for analyzing a pixelated functional map of one or more tissues of a current patient, according to an embodiment of the present invention.

Reference is now also made to FIG. 2, which is a flowchart of a method for analyzing a pixelated functional map of one or more tissues of a current patient, according to some embodiments of the present invention.

As described above and shown at 201, the reference patient database 102 manages a plurality of reference images each associated with a plurality of biological activity indications. Then, as shown at 202, a source image that includes a pixelated functional map is received. The source image is associated with a plurality of biological activity indications, as further described below. The input unit 101, which may be installed on a terminal, such as a personal computer or a server, is designed to receive the source image 104 either directly from a medical imaging system or indirectly via a content source. A medical imaging system comprises imaging by a modality, such as a PET, a PET-CT, a single photon emission computed tomography (SPECT), an extracorporeal gamma scan, an extracorporeal beta scan, an intracorporeal gamma scan, an intracorporeal beta scan, and output of a camera, such as disclosed in U.S. patent application Ser. No. 11/607,075, filed Dec. 1, 2006; U.S. patent application Ser. No. 11/034,007, filed Jan. 13, 2005; U.S. patent application Ser. No. 09/641,973, filed Aug. 21, 2000; PCT Patent Application No. PCT/IL2006/000562, filed May 11, 2006; PCT Patent Application No. PCT/IL2006/001291, filed on Nov. 9, 2006; PCT Patent Application No. PCT/IL2006/000840, filed Jul. 19, 2006; PCT Patent Application No. PCT/IL2006/000834, filed Jul. 19, 2006; PCT Patent Application No. PCT/IL2006/000059, filed Jan. 15, 2006; PCT Patent Application No. PCT/IL2005/001215, filed Nov. 16, 2005; PCT Patent Application No. PCT/IL2005/001173, filed Nov. 9, 2005; PCT Patent Application No. PCT/IL2005/000575, filed Jun. 1, 2005; PCT Patent Application No. PCT/IL2005/000572, filed Jun. 1, 2005; PCT Patent Application No. PCT/IL2005/000048, filed Jan. 13, 2005; and PCT Patent Application No. PCT/IL03/00917, filed Nov. 4, 2003; Israel Patent Application No. 172349, filed Nov. 27, 2005; and Israel Patent Application No. 171346, filed Oct. 10, 2005. The contents of all of the above documents are incorporated by reference as if fully set forth herein. A content source may be a PACS server, a PACS workstation, a computer network, or a portable memory device such as a DVD, a CD, a memory card, etc. The content source hosts and optionally allows the access to various multidimensional patient profiles, or dimensions thereof.

Optionally, the source image 104 comprises two or more functional images depicting the same tissues in the patient's body. The reference patient database 102 comprises references images each comprises two or more functional images depicting respective tissues in a body of another patient. Optionally, the functional images 104, 105 are pixelated. The functional images are optionally produced by radioactive emission. A functional image may be based on radiation emitted from radioactive tracers, such as gamma-emitting radiopharmaceuticals, which are injected into the body of the patient. The uptake of tracers is different between different tissues and between healthy, defective, and tumor tissues. Such an uptake, which is reflected by the radiation emitted from each tissue, is used for evaluating a biological activity, such as a metabolic activity of body tissue. For example, a functional image may image cardiac rhythm or respiratory rhythm, tissue metabolism, blood flow, evaluation of coronary artery disease, receptor binding, brain perfusion, and liver activity. Other indications of biological activities or inactivities that may also be depicted in a functional image may be based on the uptake rate of tracers in the related one or more tissues of the patient. Since the uptake rate of tracers is different between a healthy tissue and a tumor and is furthermore different between malignant and benign portions of a tumor, functional images or maps are of importance in tumor localization and volume determination, and especially, localization and volume determination of malignant portions of tumors.

Optionally, the functional image is a 3D medical image or a sequence of 3D medical images, such as a sequence of PET-CT, SPECT, and/or Gamma scan images that comprises a plurality of voxels. In such an embodiment, the one or more functional images provide information about a plurality of biological activities in each voxel of the source image 104. For example, each voxel may be associated with the uptake rate of a number of different tracers, such as iron isotopes, In-111 chloride, and Tc-99m labeled colloids (7-10). This use of multi-dimensional data, covering domains such as spatial/ organs, variety of tracers, and time variation, allows obtaining properties of the underlying biological processes and conclusions related to the clinical condition. Furthermore, even if a radiation, which is emitted from a certain isotope, has an imperfect specificity, the combination of its radiation with radiations of other isotopes may have a specificity that allows the agent that receives the outputs of the matching system to diagnose the pathology of the imaged tissues in the received source image.

Optionally, the biological activity or inactivity is documented as a value representing the interception of rays, such as gamma rays, which are emitted indirectly from the respective area, optionally by a positron-emitting radioisotope, which is introduced into the body on a metabolically active molecule.

Each one of the source images is optionally associated with medical information that is related to the patient. In such an embodiment, for each of some or all of the reference images 105 is associated with related medical information of a patient that her organs are depicted in the related reference image 105. As used herein, medical information means, inter alia, information which is related to the patient, such as laboratory results, therapeutic procedure records, clinical evaluations, age, gender, medical condition, ID, genetic information, patient medical record, data indicating of metabolism, blood pressure, patient history, sensitivities, allergies, different population records, treatment methods and the outcome thereof, epidemiologic classification, and patient history, such as treatment history. Optionally, each one of the source and reference images 104, 105 is optionally associated with previous and/or current structural and/or functional images of respective one or more tissues. Optionally each one of the previous images is associated with information that indicates a diagnosis thereof, a list of pathological and/or biological indications, and selected treatments and/or medicaments.

Other important features, such as 3D affine transformation descriptors may also be associated with the source image. The input unit 101 is optionally adapted to interface with more than one content source.

Optionally, the input unit 101 preprocesses the source image 104 before it is forwarded to the analysis unit 103 and/or stored in the reference patient database 102. Preferably, the source image 104 comprises a pixelated functional image that is preprocessed according to the requirements of the analysis unit 103. In one embodiment of the present invention, the pixelated functional image is denoised and/or enhanced using commonly known edge preserving filters before it is forwarded and optionally stored.

As described above, the source image 104 may be associated, or allowing the matching system 100 to associated it, with medical information of a related patient. In such an embodiment, each one of the pixelated functional images, which are hosted in the reference patient database 102, is also associated with related medical information. The reference patient database 102 may also store a number of prototypes of pathological biologic activities and/or indications, for example a pixelated medical map of one or more tissues that depicts an emission of an accumulation of radioactive glucose fluorodeoxyglucose (FDG) in an exemplary cancerous tissue.

For brevity, one or more of the reference images 105 and/or medical information, which are related to a certain patient and/or a certain patient prototype are referred to as a multidimensional patient profile. In such an embodiment, each dimension of the multidimensional patient profile provides information about a biological activity and/or indication in one or more voxels of a functional image or optionally medical information that is related to the patient that one or more of her organs are depicted in the functional image. For example, a dimension may be a functional image that images an emission of a tracer from a biological activity of one or more tissues.

Optionally, the multidimensional patient profile 104, 105 includes a pathologic classification, a clinical stage, and optionally a prognosis of such a pathologic classification. Optionally, one or more of the multidimensional patient profiles 104, 105 are associated with one or more therapies. Each therapy is associated with a related success rate value.

Optionally, the pathologic classification or other diagnosis and/or classification that is associated with the multidimensional patient profile 104, 105 and/or included therein is tagged with a reliability score that reflects the skills of the agent that provided it, the reliability of the organization which is associated with the agent, and/or the reliability of the study from which the data is taken. As used herein an agent means a physician, a measurement device, a measurement system, an imaging device, an imaging system, and an organization means a laboratory, a hospital, a medical service, an association of hospitals and/or laboratories, a geographic location of hospitals and/or laboratories, a manufacture of an agent and/or the training center that trained the agent.

Optionally, the reference patient database 102 hosts a plurality of respective functional images. In such an embodiment, each voxel of each reference image 105 is associated with a plurality of related biological activities. In such a manner, the analysis unit 103 may match between each voxel of the source image 104 and voxels of one or more of the reference images 105, which are optionally respective thereto. In an exemplary embodiment of the invention, the reference patient database 102 hosts more than a 5,000 of functional images each, of an actual patient or a known and explicit profile. Optionally, each functional image is stored along with medical information, optionally as described above, and may be referred to as a multidimensional patient profile. Each dimension in the multidimensional patient profile is the biological activity in one or more voxels of the functional image or a medical information datum.

Optionally, the multidimensional patient profile includes a respective structural image, which is optionally registered with one or more of the related functional images. The structural image is produced by reflections of penetrating rays from the internal tissues of the respective organs of the patient. Such a structural image may be produced, for example, by x-ray, CT, ultrasound, and MRI scans, which provide structural map of the internal tissues of the patient.

Optionally, the number of multidimensional patient profiles 105, which are stored in the reference patient database 102, is greater than 5,000, 50,000, 500,000, 1,000,000, 10,000,000, 100,000,000, 1,000,000,000, or intermediate values. The size of the database may be affected by the standard deviation of the records and the variance of the records. Optionally, the number of different patients whose has a multidimensional patient profile in the reference patient database 102 may be of a similar magnitude. Optionally, 5, 10, 100, 1000 or more separately identifiable functional images are provided per multidimensional patient profile in the reference patient database 102. The number of dimensions analyzed in each multidimensional patient profile may be, for example, 5, 10, 20, 40, 100, 1000, or greater or intermediate values.

The reference patient database 102 is optionally distributed in a number of servers or other hosting computing units, for example 10, 50, 100, 1000, or intermediate or greater numbers of hosting computing units. The connections between these servers are optionally secured in order to maintain data safely and privacy. Optionally, the technical specification of the system varies according to the resolution of the functional images, the number of records in the reference patient database, and the number and/or distribution of the input units 101. For example, larger images and multidimensional patient profile with more dimensions may need more bandwidth, calculating power, and storage. Optionally, in order to increase the robustness if the reference patient database, each record is stored more than once, optionally in a number of different servers which are optionally distributed in different geographical locations. Clearly, by maintaining a number of copies, the degree of data security increases and the latency of storing and retrieving the data decreases.

As described above, the source image may be received with respective medical information. This combination may be referred to as a new multidimensional patient profile. Optionally, the new multidimensional patient profile is stored for future use. Optionally, the input system comprises an integration module for integrating different modalities, such as functional and structural images from different imaging systems, for example, MRI systems, CT systems, Ultrasound (US) systems, and X-ray based systems that contain multiple dimensions and/or markers. Optionally, the integration module is designed for converting data format in an automated and/or semi-automated manner. The conversation allows the analysis unit 103 to handle data from various data sources. Optionally, the integration module is designed for registering the source image according to predefined model that has been used for registering the respective reference images. Such a registration can substantially reduce the computational complexity of the matching process.

The analysis unit 103 is designed to match between the source image 104, or the new multidimensional patient profile 104, and a plurality of respective reference images 105, or a plurality of multidimensional patient profiles 105, which are stored in the reference patient database 102. As shown at 203, after the source image is received at the analysis unit 103, a matching set of the reference images is identified by matching between the plurality of the first and second biological activity indications. The matching allows identifying a set of the hosted multidimensional patient profiles 105 that a plurality of common biological activities and/or pathogenic indications with the new multidimensional patient profile 104.

Optionally, the analysis unit 103 gives each member of the matching set a potential relevance value that is determined according to the potential relevance thereof to the new functional image and/or to the new multidimensional patient profile 104. Optionally, the potential relevance value is determined according to the proximity of the parameters that represent common biological activity indications in the members of the matching set.

The matching between the source and the reference images may be based on topological similarities between the source image and the reference images. Such a matching allows the agent to identify a matching set of multidimensional patient profiles that includes a number of common biological activities and/or indications with the patient that is depicted in the source image. The aforementioned matching allows the detection of a matching set that have a common radiation emission pattern with the source image. For example, in functional imaging of one or more brain activities, it is possible to match between emission patterns that may account as normal or abnormal functional properties of one or more regions, normal or abnormal dependencies between the one or more regions, and pathologies associated with malfunctions of biological pathways in the one or more regions. Matching such an image emission pattern may be used for classifying the new multidimensional patient profile.

In some embodiments of the present invention, the source and the reference images are optionally registered and matched according to known registration and matching methods and process. For example, see A. Venot, et al. Automated Correction of Patient Motion and Gray Values Prior to Subtraction in Digitized Angiography, IEEE Transactions on Medical Imaging, vol. MI-3, no. 4, 1984, pp 179-186; G. Malandain et al., Matching of 3D Medical Images with a Potential Based Method, IRIA, no. 1890, 1993, pp 1-37; L. R. Schad, et al., Three Dimensional Image Correlation of CT, MR, and PET Studies in Radiotherapy Treatment Planning of Brain Tumors, Journal of Computer Assisted Tomography, vol. 11, no. 6, 1987, pp 948-954; B. L. Holman, R. E. Zimmerman, et al., Computer-Assisted Superimposition of Magnetic Resonance and High-Resolution Technetium-99m-HMPAO and Thallium-201 SPECT Images of the Brain, The Journal of Nuclear Medicine, vol. 32, no. 8, 1991, pp 1478-1484; B. A. Birnbaum et al. Diagnosis with Fusion of MR, CT, and Tc-99m-labeled Red Blood Cell SPECT Images, Radiology, vol. 181, no. 2, 1991, pp 469-474, which are incorporated herein by reference.

Optionally, the new multidimensional patient profile 104 and the plurality of multidimensional patient profiles 105 include an electrophysiological reading that measures an electrical activity of one or more tissues of the related patient along a period. Optionally, the electrophysiological reading includes one or more electrophysiological readings, such as electrocardiography reading, electroencephalography reading, electrocorticography reading, electromyography reading, electrooculography reading, electroretinography reading, and electroantennography reading.

Optionally, the matching between the new multidimensional patient profile 104 and the plurality of multidimensional patient profiles 105 may include an additional or an alternative phase of matching between electrophysiological readings. Such a matching allows the user to identify a matching set that includes multidimensional patient profiles that have electrophysiological readings, which are substantially similar to the electrophysiological readings of the probed patient.

It should be noted that an arrhythmia, such as atrial fibrillation, one or more ectopic regions in the heart, an ischemia, changes in existence of biochemical channels which are part of the electrical conduction system, for example connexin-42, and/or changes in the activity and/or concentration of intracellular and intercellular calcium handling proteins, usually have a known electrocardiography reading pattern.

The aforementioned matching allows the detection of a matching set of multidimensional patient profiles that have a common electrophysiological reading with the new multidimensional patient profile. Such a common electrophysiological reading may be used for classifying and/or diagnosing the new multidimensional patient profile and/or alarming the user of the matching system 100 about a possible detection of one or more pathologies which have been identified in members of the matching set.

In one embodiment of the present invention, the source and at least some of the reference images are four-dimensional (4D) medical images of an organ, such as the heart. A 4D medical image is a data set composed of a time-series of 3D medical images that reflects the behavior of the depicted tissue during a certain period. In such an embodiment, the reference and the source images, which may also be known as kinetic images, may be correlated before they are matched by the analysis unit 103. Matching a 4D medical image may be important in organs such as the heart wherein the shape of the organ substantially change over time and can provide information about the pathological level thereof.

In such an embodiment, the matching that is performed by the analysis unit 103 may be performed with respect to the time domain. Such systems, methods, and associated tools may be applied to cardiology, oncology and brain imaging with novel imaging systems, including for example with the nuclear imaging technology presented by Spectrum Dynamics in International Application No. WO2006/051531 published on 18 May 2006 that is incorporated herein by reference.

As described above, each one of the multidimensional patient profiles 104, 105 may comprise medical information, such as medical history, about a related patient. Such information, as described above, may comprise personal information about the patient, such as his or her age, gender, and physical condition at the time the scan has been held. As the differences between biological indications of patients with different medical condition and/or history are substantial, such information may be important, in some embodiments, in order to output efficient recommendation, treatment guidelines, or matching set that can be used by the physician, optionally as described below. For example, it is clear that low red and/or white blood cell count has different meaning if the patient is treated with chemotherapy for cancer or not.

Optionally, an initial diagnosis, which is performed by an agent or attached to the new patient profile, is also included. Such medical information may also be used as another dimension in the multidimensional patient profile 104 for the analysis of the source image, as described below.

Optionally, the matching that is performed by the analysis unit 103 is based on processing the data in the multidimensional patient profiles 104, 105. Optionally, the analysis unit 103 processes the data in order to detect interactions and/or complex biological processes that may last for a certain period. For example, the analysis unit 103 may correlate between a timeline that describes the variability of one or more biological and/or pathological indications in the new patient profile and a respective timeline in the multidimensional patient profile which are hosted in the reference patient database.

Optionally, the measuring includes applying one or more of a variety of statistical and network analysis techniques to one or more dimensions of the multidimensional patient profile. Such an analysis may include an analysis of gene expression, proteomics, transcriptomics, gene regulatory network, metabolic pathways, and/or cellular signaling. For example, the analysis unit 103 may measure an absolute concentration of proteins and/or messenger ribonucleic acid (RNA) of a specific type and a specific state, such as phosphorylated mRNA, glycated mRNA, and various protein conformations. The detected and/or measured data is matched with respective interaction and/or measurements in the multidimensional patient profiles 105 of the reference patient database 102.

In such an embodiment, a multidimensional patient profile includes sequential data of biological activities that is optionally based on dynamic and/or static properties of one or more tracers. The biological activities may have time dependency among them. For example, an uptake of one tracer that is followed by an uptake of a subsequent uptake of another tracer may be indicative to the existence of a time-dependency between two biological activities and potentially to the understanding that one biological activity is the cause and/or a part of the cause of another biological activity and may be associated with a certain pathological indication of the patient. Optionally, the data in the reference patient database 102 is arranged in data tables, which support the aforementioned measurements and interactions.

Optionally, the reference patient database 102 hosts at least 5,000 multidimensional patient profiles. Each one of the multidimensional patient profiles comprises information about the patient from various evaluation and imaging systems and agents, such as one, two, three, four or more of epidemiologic, genetic, functional, chemical, and treatment related information. Matching the new multidimensional patient profile 104 with the multidimensional patient profiles 105 may yield one or more matching sets. Each member of a certain matching set has a combination of biological activities and/or indications that is common to all the members of the certain matching set. The relation between the biological activities and/or indications in this combination may not be obvious to the common physician or even known from the medical literature. Thus, the matching system 100 that optionally automatically match between the new multidimensional patient profiles 104 and the multidimensional patient profiles 105 can detect combinations that include relations between various biological activities which are not obvious or known to the agent that diagnoses the patients with the new multidimensional patient profiles 104.

As the matching is performed with a large scale of multidimensional patient profiles, fuzzy logic methods may be used for identifying the matching set. As commonly, known fuzzy logic is derived from fuzzy set theory dealing with reasoning that is approximate rather than precisely deduced from classical predicate logic, see Klir, George J.; St Clair, Ute H.; Yuan, Bo (1997). Fuzzy set theory: foundations and applications. Englewood Cliffs, N.J.: Prentice Hall. ISBN 0133410587 and Klir, George J.; Yuan, Bo (1995). Fuzzy sets and fuzzy logic: theory and applications. Upper Saddle River, N.J.: Prentice Hall PTR. ISBN 0-13-101171-5, which are incorporated herein by reference.

As described above and shown at 204, after the source image is received at the analysis unit 103, a matching set of the reference images is identified by matching between the plurality of the first and second biological activity indications. Optionally, the matching is performed between predefined ranges which are set around the values given at the multidimensional patient profile 104. As described above, the multidimensional patient profile 104 comprises different values that represent medical information and biological indications which are related the patient. In such an embodiment, as the matching is between predefined ranges and not according to discrete values the intersecting group may include profiles of patients which are not exactly as the profile of the current patient.

Optionally, the matching of each one of the values and/or the ranges of the patient profile is weighted according to an estimation that reflects the importance. For example, a potential relevance between biological indications such as hemoglobin, hematocrit, and/or iron level measurements may receive a higher weight than the weight that is given to the height or the gender of the patient.

Optionally, a weight is given to a ratio or any other function that is based on a number of values and/or the ranges of the patient profile. For example, the ratio of hemoglobin weight to hematocrit is given with a high weight. Such a ratio distinguishes the normally colored cells from paler cells to classify different anemias and aid in determining cause.

Optionally, the weights are dynamic and depend on other values such as the treatment that is given to the patient, the age of the patient, his medical history, and/or his medical condition.

As shown at 204, after the matching set has been identified it is used for image data acquisition, diagnosis of the source image, calculation of treatment guidelines, and/or classification of the source image. The matching set may comprise multidimensional patient profiles of patients with similar biological activities and/or indications that receive successful treatments and with multidimensional patient profiles of patients with similar biological activities and/or indications that receive unsuccessful treatments. Such matching sets may be useful for allowing the physician to select one or more method of treatments, to optimize and/or to reduce the radiation doses to which the patient is exposed, and to optimize and/or to reduce a medicament dose that the patient receives.

Optionally, a reference patient database 102 with more dimensions allows the matching of more combinations of different dimensions and/or interactions between different biological activities. Such a matching may be used for detecting combinations and interactions, which are not intuitive or based on the known studies and/or tests. Such a multidimensional data analysis may be performed using differential equations and/or control theory methods, as applicable to dynamic systems such as a biological entity, for example the human body.

As described above, the matching system 100 is designed to receive a source image and optionally medical information from an imaging system and/or a storage system and to match it with the reference images and/or other records of the reference patient database 102. As the functional image is optionally matched with large scale of multidimensional patient profiles and optionally processed and analyzed for the identification of complex biological processes that may last for a certain period, the quality of thereof may be relatively low, for example a functional image with high levels of noise. Optionally, the matching system 100 allows using imaging cameras with a relatively low number of detectors, such as a hand-held imaging camera that is designed for capturing images during a data-responsive scanning, to perform a real time reconstruction, and to determine in real time whether additional data is needed to achieve a match, as described above.

Optionally, the analysis unit 103 uses information that is found in the matching set to complete, to denoise, to calibrate, and/or to change areas in the received source image.

It should be noted that using such a matching system 100 may assist particularly in standardizing the analysis of functional images and generally in standardizing the analysis of multidimensional patient profiles. As commonly known, not all the physicians have a common set of guidelines for diagnosing a functional image or many other variants of a patient profile. For example, while a certain physician checks the hippocampus region for diagnosing early Alzheimer's dementia, another physician may check other regions of the brain, such as the medial temporal lobes and the anterior cingulate. In particular, such the matching system 100 may be used for assuring that certain biological activities and indications are probed whenever a functional image or any other variant of a patient profile is diagnosed and/or classified by a physician, such as a general radiologist.

Optionally, the reference patient database 102 is used by the analysis unit 103 for classifying pathological indications that have more than one visible and/or measurable characteristics and not a clear surrogate marker. Optionally, the reference patient database 102 may be used for detecting and/or anticipating the occurrence of a heart failure. Such a detection and/or an anticipation may by based on various biological activities which are documented in the multidimensional patient profiles, including but not limited to echocardiography, blood tests, cardiac mapping, which is optionally isotope based, anatomical information, for example from CT and/or angiography procedures, quality of life questionnaires, electrophysiology parameters, etc.

In one embodiment of the present invention, the matching system 100 is used for solving an inherent problem of the SPECT image analysis. A 3D imaging system, such as SPECT system, assesses a relative decrease in the uptake of a tracer in a certain region by comparing the uptake thereof with the uptake of other regions. The uptake is determined according to the rate of reduction in the emission flow. Such a comparison may be used for detecting regions with stenosis that is relatively high in relation to other regions. It is more difficult, and sometimes impossible, to detect milder stenosis in other regions of the functional image. As described above, the analysis unit 103 is designed for matching a SPECT image with other images. In such an embodiment, each region in the image is compared with respective regions in other SPECT images. In such a manner, the uptake of one region is matched against the uptake in a respective region and not against the uptake of other regions in the same image. Such a matching may provide pathological information that would have gone unnoticed in a commonly used diagnosis. It should be noted that a comparison, such as the aforementioned comparison, is between absolute values taken from respective regions and therefore provide a more accurate outcome than the commonly practiced comparison that is performed between relative values taken from different, unrelated regions.

Figure 3:
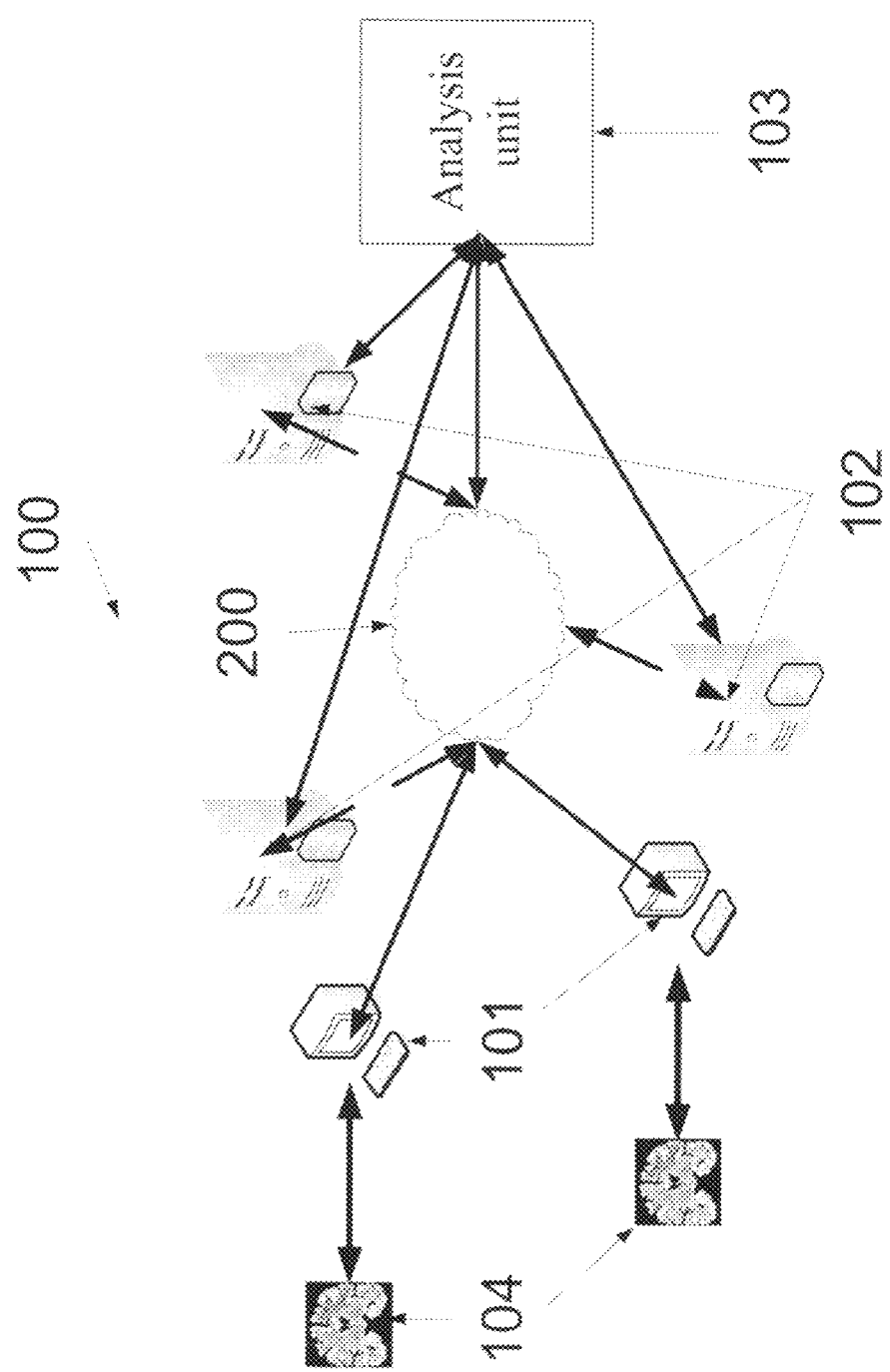
FIG. 3 is a schematic illustration of a distributed matching system for analyzing a medical map of one or more tissues, according to one embodiment of the present invention.

Reference is now also made to FIG. 3, which is a schematic illustration of a distributed matching system 100 for analyzing a medical image and/or a map of one or more tissues, according to one embodiment of the present invention. The matching system 100 comprises the input unit 101, the reference patient database 102, and the analysis unit 103 which are depicted in FIG. 1. However, in FIG. 3, the system is a distributed system that comprises a number of input units 101 and optionally a distributed reference patient database 102. In such an embodiment, each input unit 101 may be installed or accessed via a different client terminal, such as a personal computer, a Smartphone, a personal digital assistant (PDA), and a laptop. The input units 101 are connected, via a computer network 200, such as the Internet, to the reference patient database 102. The reference patient database 102 is optionally distributed among a plurality of different storage devices, such as a plurality of servers 102. The input units 101 and the storage devices of the distributed reference patient database 102 are connected to the analysis unit 103 via the computer network 200.

In such an embodiment, each one of the client terminals 101 may be used for adding a new patient profile 104 to the reference patient database 102 and/or for forwarding it to the analysis unit 103 for analysis, for example as further described above.

Optionally, the matching system 100 is connected to one or more user interfaces (UIs), which are optionally installed in one or more of the client terminals 101. Each UI allows one or more of the users to extract statistical information from the reference patient database 102. Such a UI may be used for producing improved understanding of the biological processes. Optionally, the UI allows the user to identify and to analyze biological pathways, cell processes, and cellular circuits based on the match between the new multidimensional patient profiles 104 and the multidimensional patient profiles 105.

Optionally, the UI is designed to display the output of the analysis unit 3. Optionally, the analysis unit 3 outputs a list of the matching multidimensional patient profiles. Optionally, the list is sorted according to the potential relevancepotential relevance values of the matching multidimensional patient profiles.

As described above, the new multidimensional patient profiles 104 may be matched with a matching set that comprises multidimensional patient profiles, which have been classified as having biological activities and/or indications of one or more pathological diagnosis. Optionally, the analysis unit 103 generates a complete tree of the one or more pathological diagnosis and/or one or more suggested treatments for each one of the pathological diagnosis and forward it for a display at the client terminal from which the new multidimensional patient profiles 104 have been received. Optionally, the tree is weighted according to the prevalence of a certain match and/or the prevalence of a certain diagnosis in the matched multidimensional patient profiles.

In such a manner, the physician receives a graphical display, such as a tree, optionally weighted, of possible diagnosis and suggested treatments. As described below, the suggested treatments may also be weighted, shown the physician the statistic of the treatment success.

As depicted in FIG. 3, the matching system 100 comprises a plurality of distributed client terminals, which are optionally located in different locations, for example in different diagnostic imaging centers (DICs). In such a manner, the system allows physicians and researchers from different locations to use the same analysis unit 103 and the same reference patient database 102 for diagnosing and/or classifying a new functional image and/or a new multidimensional patient profile. The system assures that these functional images and/or new multidimensional patient profiles are matched against the same multidimensional patient profiles, regardless to their origin.

Optionally, as described above, the matching system 100 is used as a research tool. Optionally, the UI allows a user to define search indicia with one or more and/or biological activities or expressions thereof. The UI instructs the analysis unit 103 to search for a match between the search indicia and the plurality of multidimensional patient profiles. Such a research tool 100 may be used for improving the understanding of the biological processes which are defined in the search indicia.

Optionally, the research tool 100 allows the user to define a genetic population, an environment, an age, a gender, a medical condition, etc. In such a manner, the user may define a test group for an experiment. Optionally, the research tool 100 allows users to upload data of test groups, which have been used in a certain experiment and/or study. In such a manner, an outcome of a future experiment, such as a sequential experiment, can be easily compared with the uploaded data of any test group. As the uploaded data is related to a number of different trials and studies, the analysis unit 103 may combine the results of several studies that address a set of related research hypotheses, generating a match, a classification, an alarm, or a diagnosis that is based on a meta-study, in which as many patients as possible participates.

As, in some embodiments of the invention, the reference patient database 102 is greater than 500,000, 1,000,000, 10,000,000, 100,000,000, 1,000,000,000, or intermediate values, numerous control and/or test groups may be defined for supporting specific combination of biological activities and/or medical information. For example, where A, B, and C denote different tracers, the matching system 100 may support a combination of an analysis with two tracers A+B, a combination with two tracers A+C, and a combination with two tracers B+C. As the number of potential tracers expands, more combinations may be possible and the number of documented pathologies increases. It should be noted that such an embodiment may be used for reducing the radiation to which a patient is exposed during a diagnosis process. The analysis may allow a physician to diagnose a biological activity based on a match with multidimensional patient profiles that has the same combination of tracers as the new multidimensional patient profile, and not based on the injection and the imaging of one or more additional tracers.

Optionally, the matched matching set is used by the physician to determine which additional examination is needed. As described above, the matching set includes patient profiles that have one or more characteristics, such as biological indications and/or medical information, in common with the profile of the patient. A segmentation of the matching set's members according to characteristics thereof, which are not in common with the characteristics of the new patient profile, can indicate which additional data is needed in order to evaluate more accurately which treatment should be given to the new patient. For example, if one segment of the matching set includes patent profiles of members with an indication of normal hemoglobin and non-pathologic diagnosis and another segment of the matching set includes patent profiles of members with an indication of low hemoglobin and a pathologic diagnosis the physician receive an indication that an hemoglobin level test is needed in order to diagnose the new patient more accurately.

Optionally, the matching system 100 is used as an adaptive system for instructing an agent during a medical operation. In such an embodiment, the agent constantly updates and/or reenters the new patient profile that is matched by the matching system 100. The matching system 100 reanalyzes the updated new patient profile and provides the physician with a new, optionally more accurate, matching set and/or treatment recommendation. In such a manner, a physician may use the matching system 100 to predict the outcome of possible outcomes of different operational actions during a medical operation.

It should be noted that matching the new multidimensional patient profile 104 with records of a database that hosts thousands of multidimensional patient profiles can substantially reduce the standard deviation of the matching set. The more multidimensional patient profiles are stored in the database the more the members of the matching set have in common with the new multidimensional patient profile 104. The reference patient database 102 comprises data that describes and/or depicts pathological biological activities and/or indications optionally in association with medical information. These records allow identifying a matching set that has members having one or more common characteristics with the new multidimensional patient profile 104. Such one or more common characteristics may not be clear or known from the known studies and/or tests. The matching is done between absolute values and based on real data that is taken from real patients and not based on processed models that usually cannot accurately reflect dynamic statistical data that is optionally constantly changed and updated with new records.

For example, the reference patient database 102 is uploaded with data collected from trials that has been performed by imaging simultaneously or sequentially a large variety of tracers, which may be referred to as a cocktail, trials that has been performed on different populations, and trials that has been performed on patients with medical information. Such data may be collected either from various studies or during the ordinary course of practicing medicine.

In such a manner, the accuracy of the matching substantially increases. If, for example, an uptake of a tracer is an indication of a certain biological activity has a specificity of ~10%, the matching of the uptake of more tracers can provide a higher specificity of ~1%.

Optionally, the reference patient database 102 is connected to other medical databases and can match between the multidimensional patient profiles and records from the other medical databases. Optionally, a multidimensional patient profile may be based on data from other medical databases.

In an exemplary embodiment of the invention, a system is provided to store and analyze all such data. It should be noted that such an uploaded data may be used for analysis, classification, alarming, and/or diagnosing, optionally as described above, and not only for research.

Optionally, the multidimensional patient profiles comprise a status record that describes the health of the related patient. If the patient has been diagnosed by the matching system 100 and/or by a physician as unhealthy patient, the status record may define an impairment of health or a condition of abnormal functioning of the patient or of one or more of the patient tissues. The multidimensional patient profiles comprise a record that describes and/or defines the treatment the patient received and a value, such as a weigh value, that defines the effectiveness of that treatment. Optionally, the analysis unit 103 is designed to suggest a therapy to the patient with is documented in the new multidimensional patient profile. In such an embodiment, the analysis unit 103 identifies a matching set of members having one or more dimensions in common with the new multidimensional patient profile. The dimensions may be medical information and/or a topological potential relevance between related functional images, optionally as described above: Optionally, the analysis unit 103 identifies which therapy has been used most successfully for recovering the members matching set, optionally using the aforementioned weight, and output a therapy suggestion or a list of weighted therapy suggestions based thereupon.

Optionally, the analysis unit 103 outputs the list of weighted therapy suggestions and/or the members of the intersecting list to a display at the client terminal from which the functional image and/or the new multidimensional patient profile has been received.

It should be noted that though the multidimensional patient profiles 104, 105 may comprise information about the diagnosis that defines the impairment of health or the condition of abnormal functioning of the patient, the analysis unit 3 may ignore that information. In such a manner, the analysis unit 103 may output a therapy suggestion or a list of weighted therapy suggestions based on medical measurements only, without combining any opinions and/or conclusions of physicians or the like.

Optionally, a dimension of the multidimensional patient profiles 104, 105 is weighted. In such a manner, common parameters may effect the suggestion according to a weight that is associated therewith.

As described above, the system allows the matching of multidimensional profiles. Such a matching may require high computational complexity. In order to provide a short response time for analyzing, classifying, and/or diagnosing requests, the aforementioned matching is performed using a processing unit that has improved processing abilities in relation to the local processors of each one of the client terminals. Optionally, the central processing unit includes multiple processing units that combines a tightly coupled parallel architecture and/or in a loosely coupled distributed architecture.

Optionally, the response time of the central processing unit allows the matching of between the source image and the reference images and/or the new multidimensional patient profile 104 and the records of the reference patient database 102 in real time. In order to provide such a response rate, the multiple processing units may be processors with high processing capacity. Optionally, the multiple processing units are adapted to access large amounts of data. Optionally, each one of the multiple processing units has a multiple data bus, preferably 64-bit or 128-bit processing power, an arithmetic logic unit (ALU), and wide range of fast I/O channels.

Optionally, the system comprises a maintenance module that includes a control mechanism for data quality and data management in order to assure the reliability and availability of the reference patient database 102. Optionally, the maintenance module assures that the records of the reference patient database 102 are kept confidential, inter alia, in order to assure the privacy of the documented patient. Optionally, the maintenance module scores the quality of each record or batch of records that are uploaded to the reference patient database 102.

As described above, the input unit 101 optionally receives a source image that comprises a functional image, as shown at 104, and forwards it for processing by the analysis unit 103 in real time. In one embodiment of the present invention, the matching system 100 is used for allowing an imaging system to have active vision. As used herein, an imaging system with active vision means an imaging system that is able to interact with the imaged scene by altering its viewpoint rather than passively observing it, and by operating on sequences of images rather than on a single frame.

Figure 4:
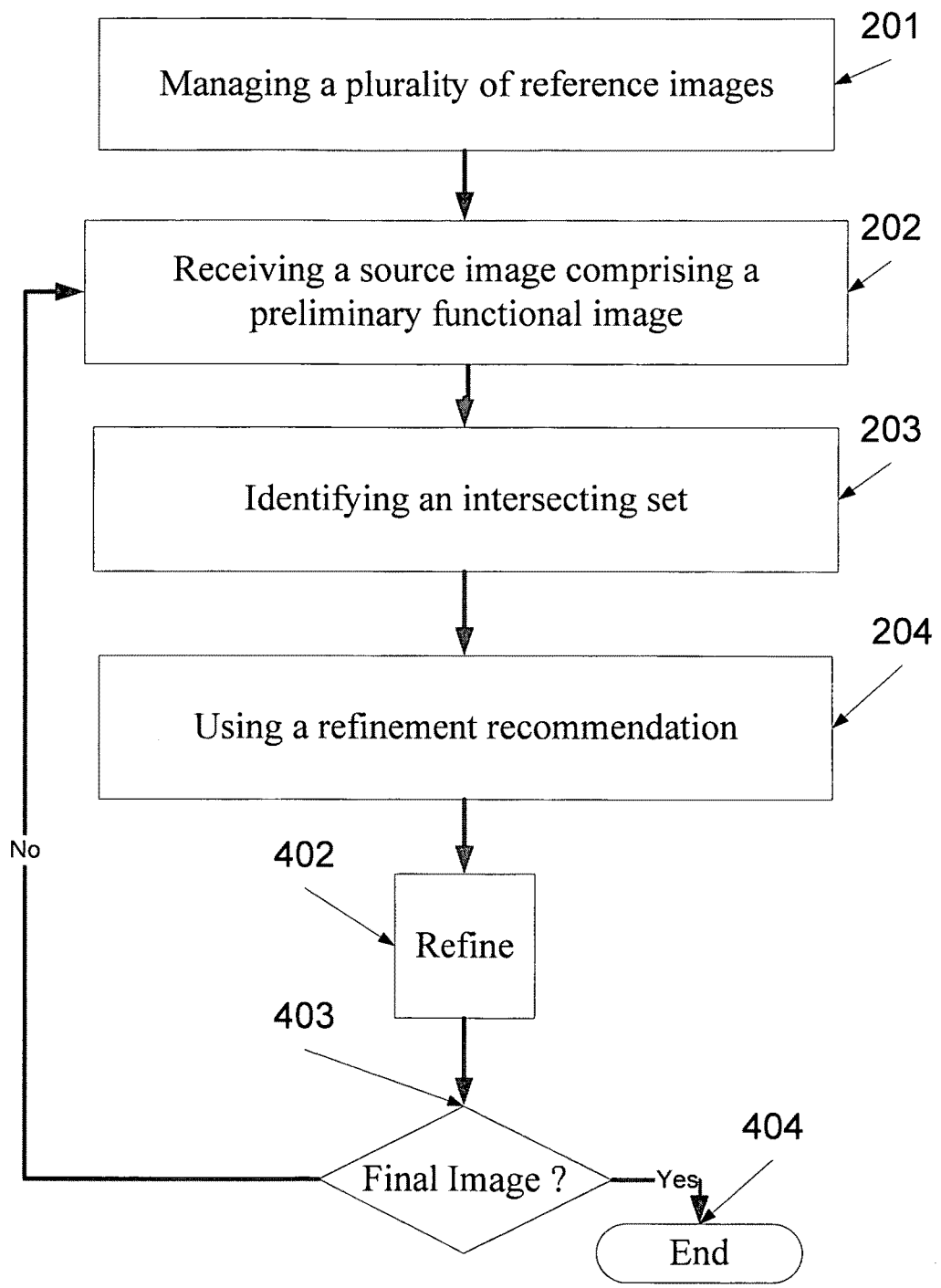
FIG. 4 is a flowchart for using the matching process that is depicted in FIG. 2 for refining the functional image, according to one embodiment of the present invention.

Reference is now made to FIG. 4, which is a flowchart for using the aforementioned matching process for refining the functional image, for example using an active vision method, according to one embodiment of the present invention. Optionally, blocks 201-204 are similar to the blocks described in FIG. 2. However, FIG. 4 further depicts blocks 401-404 and the received source image comprises 401 is a preliminary functional image and not a final functional image. As depicted, after the received preliminary image is received, a matching set is identified, optionally as described above. Then, as shown at 204, a recommendation and/or is calculated and used for refining the image and/or a diagnosis that is based on the recommendation, as shown at 402. As shown at 403, the depicted process is repeated as long as the refined image and/or the patient profile diagnosis are not final or for a predefined number of iterations. Optionally, an image is classified as final according to user instructions, the identification of a matching set having a predefined size, and the like.

Optionally, such a process is used for repositioning the radiation detectors of the imaging system or determining the scanning pattern thereof, thereby improving the acquisition of parameters such as energy resolution, field of view, and/or scan pattern. The matching set, which is produced by the analysis unit 103, comprises a number of images that depicts respective tissues and optionally neighboring tissues. These images depict areas in which there may be irregular biological indications and/or pathological indications. Optionally, the analysis system identifies these irregularities by matching the members of the matching set with a model of a normal image and directs the radiation detectors of the imaging system toward these areas.

Optionally, such a process may be used for generating a continuous motion or step-wise motion for a set of detectors. As described above, the preliminary functional image is matched with a plurality of reference images. Such a matching may reduce the amount of radiation to which a patient is exposed, optionally by reducing the size of the area that is imaged. For example, if the matching set comprises one or more reference images with a certain pathological indication in a certain area, the analysis unit 103 outputs a refinement recommendation that directs the detectors toward another area that allows the analysis unit 103 to determine how to diagnose the pathological indication.

Optionally, a certain area is imaged using a limited number of detectors that sequentially scan sub-areas thereof In such an embodiment, the preliminary functional image, which is received at 202, is an image of one of the sub-areas. By analyzing the acquire data at a certain given time point, the matching set is used as shown at 203 and the next sub-area to be scanned is defined for the next time point. Such a closed loop imaging may be performed in a magnitude of scale of minutes, seconds, and fractions of seconds, such as $\frac{1}{100}$th or $\frac{1}{1000}$th of a second. Such an embodiment allows the detection of an onset of a biological activity, such as an arrhythmia or a brain activity, and may be used for adapting the scanning pattern according to the propagation and development of the onset.

In order to facilitate such an active vision, the reference images may include preliminary functional images, which are partially reconstructed images that have been taken during the acquisition thereof and/or of one or more segments of a certain area which is respective to the probed area.

Such an embodiment allows the imaging of a complex static scene in nonuniform resolution, thereby reduces the computational complexity of the imaging.

As described above, the process that is depicted in FIG. 4 allows refining the final functional image, according to one or more preliminary functional images. Such a refinement may be understood reconstructing certain regions of interest (ROIs) of the final functional image to higher resolution and other ROIs to lower resolution, thereby reducing the scanning time and/or the radiation dosages. It should be noted that resolution may be understood as a spatial resolution, a temporal resolution or both. The functional image reconstruction may require an analysis of intensities or other parameters which are associated with intensities in a high numbers of variables.

Optionally, the reconstruction is performed in a voxel-by-voxel approach. The reconstructed variables are analyzed, fixed, and then further analyzed in a set of repeated steps, for example as depicted in FIG. 4. A sub-group of voxels is selected, the voxels' values are refined, and the process is reiterated with other sub-group. In an exemplary embodiment of the invention, this approach is implemented using a parallel processing architecture, for example, reconstructing different voxels in parallel.

In an exemplary embodiment of the invention, the refinement recommendation includes instructions that define which ROI to scan next. Optionally, the refinement recommendation is based on an analysis that is provided from a matching set that suggests progression in patients with similar patient profile.

Possibly, the computation power that is used to analyze such a progression in real-time is high and may require a specialized computational system architecture. As described above, the analysis unit 103 may comprise a processing unit that includes multiple high speed CPUs and/or data processing systems (DPSs) that implement multiple data buses and/or 64 bit, 128 bit, and/or stronger CPU architectures.

Optionally, the refinement recommendation may be a selection of a new viewpoint and/or view parameters for one or more of the aforementioned detectors.

Optionally, the reference patient database 102 hosts a probability matrix, such as probability vector that define the probability that a photon emitted from points in space would be detected by the detector for each viewpoint. Such probability matrixes are used as part of the algorithms for estimating the detected photon counts from estimated intensities, and for other algorithmic steps.

Optionally, the reconstruction includes reconstruction of parameters associated with time-varying biological processes. In such an embodiment, some of the processes may require non-linear modeling of the process. In one embodiment, the matching system 100 allows the reconstruction of these parameters in real time, allowing a medical team to diagnose a patient or the progress of a therapeutic procedure immediately.

Optionally, the matching system 100 is designed to optimize the number of views which are necessary to obtain enough information for imaging by identifying when and/or where to acquire a certain preliminary image. As mentioned above, a certain biological activity may be an outcome of another biological activity. In such an embodiment, the biological activities that provide pathological indications may appear in a sequential manner and therefore the ROI should be defined in different locations at different time slots. Furthermore, if the reconstructed parameters are kinetics parameters, such as order of reaction, kinetic rate constant, apparent, intrinsic and diffusional activation energies and activation energy (Ea), the scanning pattern is planned according to an anticipated time curve. Optionally, the anticipated time curve is adjusted in real time.

In an exemplary embodiment of the present invention, the amount and/or complexity of the data that is acquired is reduced to enable easier image processing, image reconstruction, and/or categorization of the disease process. Information maximization and need to reduce complexity of procedure may be addressed in this approach. It may further allow reducing the volume of the relevant and essential data that is needed for making efficient use of resources, such as computational and/or storage resources.

It is expected that during the life of a patent maturing from this application many relevant systems and devices will be developed and the scope of the term a voxel, a pixel element, a patient profile, an imaging device, CT, MRI, and SPECT are intended to include all such new technologies a priori.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of medical imaging, comprising:
providing a reference database of medical pathology images and information about a plurality of first biological activity indications associated with said respective pathology images;
receiving a preliminary nuclear medical image derived from a patient together with information about a plurality of associated second biological activity indications, said preliminary nuclear medical image being a mapping of radiation emitted from a first tracer;
identifying a match between one or more images in the reference pathology database and the preliminary medical image using a computing device to compare said plurality of second biological activity indications and one or more of said first biological activity indications;
wherein said comparing is performed between predefined ranges which are set around values given at a multidimensional patient profile and wherein said comparing of each one of the values and/or ranges is weighted according to importance; and
automatically generating a recommendation acquisition or further patient images of radiation emitted by a second tracer at locations based on said identified match,
wherein each said first and second plurality of biological activity indications comprises an uptake level of radiation emitted from a plurality of tracers.

2. The method of claim 1, wherein said received medical image is associated with first medical information related to the current patient, and each said reference medical images are associated with second medical information, said matching comprising matching between said first medical information and said second medical information.

3. The method of claim 1, wherein said received and reference medical images are pixelated.

4. The method of claim 3, at least some pixels of said received pixelated medical image are associated with said plurality of second biological activity indications, at least some pixels of each said pixelated medical image are associated with said plurality of first biological activity indications.

5. The method of claim 1, further comprising preprocessing said received medical image before identification of said one or more matching reference images, said preprocessing comprising a member of a group consisting of: registering said received medical image according to at least one of said reference medical images and de-noising said received medical image.

6. The method of claim 1, wherein each said received and reference medical image is a functional map that that is obtained by one of a group consisting of: a positron emission tomography (PET), a PET—computerized tomography (CT), a single photon emission computed tomography (SPECT), an extracorporeal gamma scan, an extracorporeal beta scan, an intra-corporeal gamma scan, and an intra-corporeal beta scan.

7. The method of claim 1, wherein said recommendation includes a diagnosis of said received medical image determined according to pathology of the identified reference images.

8. The method of claim 1, wherein said reference image database includes more than 1,000,000 medical images derived from a plurality of patients.

9. The method of claim 1, wherein said identification comprises matching topological similarities between said received medical image and at least one of said plurality of reference medical images.

10. The method of claim 1, wherein said identification comprises matching common radiation emission patterns between said received medical image and at least one of said plurality of reference medical images.

11. The method of claim 1, wherein said received medical image and at least one of said plurality of reference medical images are kinetic medical images.

12. The method of claim 1, wherein at least one of said reference medical images is associated with a method of treatment and with a success evaluation thereof for a particular pathology, and further comprising automatically outputting a treatment recommendation according to a pathology associated with one or more of the identified reference images.

13. The method of claim 1, further comprising identifying a plurality of biological pathways in said received and reference medical images respectively according to said first and second plurality of biological activity indications, wherein identification of said matching reference images is based on matching said plurality of biological pathways.

14. The method of claim 1, wherein said reference and received images are processed in real time.

15. The method of claim 1, wherein at least one of said plurality of medical images and said received medical image are of the patient.

16. A method according to claim 1, wherein at least one of said first biological activity indication and at least one of said second biological activity indications are the same.

17. A method according to claim 1, wherein at least one of said first biological activity indication and at least one of said second biological activity indications are different.

18. A method according to claim 1, wherein said plurality of medical images are images of a plurality of patients.

19. A method according to claim 1, further including acquiring at least one additional image of the patient based on the recommendation.

20. An imaging system for capturing a medical image of at least one tissue of a patient, comprising:
  at least one nuclear emission detector for obtaining a source medical image of the patient associated with at least one first biological activity indication;
  a computer database configured for storing a plurality of reference medical pathology images including images corresponding to a plurality of pathologies, each with an associated second biological activity indication; and
  a computing device configured to provide image processing of the reference and source images and to identify one or more reference images matching said source medical image by comparing said first and second biological activity indications;
  wherein said comparing is performed between predefined ranges which are set around values given at a multidimensional patient profile and wherein the comparing of each one of the values and/or ranges is weighted according to importance
  said computing device being further configured to provide an output for instructing image data acquisition performed by said at least one detector according to said identified matching set,
  wherein said source medical image is a preliminary image mapping radiation emitted from a first tracer and said output unit provides a recommendation for a protocol of image acquisition of radiation emitted by a second tracer based on said identified matching set,
  wherein each said first and second plurality of biological activity indications comprises an uptake level of radiation emitted from a plurality of tracers.

21. The system of claim 20, wherein said source medical image depicts a segment of a requested area, said output instructing the maneuvering said at least one detector to capture an additional segment of said requested area according to said matching.

22. The system of claim 20, wherein said detector comprises a radiation transmitting unit for emitting radiation toward said segment, and said output instructs adjusting the intensity of said emitted radiation according to said identified matching images.

23. The system of claim 20, wherein said detector is configured for obtaining said medical image, by a first modality, selected from the group consisting of a single photon emission computed tomography (SPECT) unit, a positron emission tomography (PET) unit, an extracorporeal, hand-held gamma scan unit, an extracorporeal unit, hand-held beta scan, an intra-corporeal gamma scan, an intra-corporeal beta scan, an intravascular gamma scan, and an intravascular beta scan.

24. A system according to claim 20, wherein at least one of said first biological activity indication and at least one of said second biological activity indications are the same.

25. A system according to claim 20, wherein at least one of said first biological activity indication and at least one of said second biological activity indications are different.

26. A system according to claim 20, wherein said plurality of reference medical images are images of a plurality of patients.

27. A method for obtaining a medical image of at least one tissue of a patient, comprising:
- receiving a preliminary nuclear medical image associated with at least one first biological activity indication, said preliminary nuclear image mapping radiation received from a first tracer;
- matching between said at least one first biological activity and a plurality of respective biological activities associated with a reference pathological medical image using a computing device;
- wherein said matching is performed between predefined ranges which are set around values given at a multidimensional patient profile, and the matching of each one of the values and/or ranges is weighted according to importance and
- outputting a recommendation for a protocol of further image acquisition from said patient of radiation emitted by a second tracer based on said matching,
- wherein each said first and second plurality of biological activity indications comprises an uptake level of radiation emitted from a plurality of tracers.

28. The method of claim 27, further comprising:
- d) obtaining said additional preliminary medical image according to said instructions; and
- e) combining said preliminary medical images producing a final medical image.

29. The method of claim 28, further comprises repeating b)-e), wherein said at least one first biological activity are taken from said final medical image.

30. The method of claim 27, wherein said recommendation comprises a member of a group comprising: an identifier defining which tracer to use during said obtaining, an identifier defining in which concentration to use a tracer during said obtaining, a point of view of at least one detector which is used for said obtaining, a region of interest to be imaged during said obtaining, and refining said preliminary medical image.

31. A method according to claim 27, wherein at least one of said first biological activity indication and at least one of said respective biological activities are the same.

32. A method according to claim 27, wherein at least one of said first biological activity indications and at least one of said respective biological activities are different.

33. A method according to claim 27, wherein said reference medical images are images of a plurality of patients.

34. A method for calculating a treatment recommendation, comprising:
- a) managing a plurality of patient profiles each being associated with a plurality of patient medical records, at least one treatment, and an outcome evaluation of said at least one treatment;
- b) receiving a current patient profile being associated with a plurality of related medical records from an image mapping nuclear radiation received from a first plurality of tracers;
- c) identifying a matching set of said managed patient profiles by matching between said plurality of patient and related medical records;
- wherein said matching is performed between predefined ranges which are set around values given at a multidimensional patient profile, and the matching of each one of the values and/or ranges is weighted according to importance and
- d) calculating a medical recommendation for a protocol of image acquisition from second plurality of tracers based on to said at least one treatment of members of said matching set,
- wherein each said first and second plurality of biological activity indications comprises an uptake level of radiation emitted from plurality of tracers.

35. The method of claim 34, wherein each said patient profile having a medical image, each said medical image being associated with a plurality of biological activity indications, said identifying comprising identifying said matching set by matching between biological activity indications of said current patient profile and said plurality of patient profiles.

36. The method of claim 34, wherein at least some of said plurality of patient medical records are associated with a time tag indicating a related occurrence or examination time.

37. The method of claim 34, wherein each said at least one treatment is associated with a reliability score, said calculating comprising calculating said medical recommendation according to said reliability score of members of said matching set.

38. The method of claim 34, wherein each said patient profile is associated with a current treatment record, said identifying comprising identifying said matching set by matching between current treatment records of said current patient profile and of said plurality of patient profiles, said medical recommendation comprising a continuation treatment for said current patient profile.

39. The method of claim 38, wherein said current treatment record profile is associated with a respective outcome evaluation.

40. The method of claim 38, further comprising:
- e) updating said current treatment record of said current patient profile with said medical recommendation and said respective outcome evaluation with an outcome of a respective treatment; and
- f) repeating a)-d) wherein said current treatment record is said updated current patient profile and said respective outcome evaluation is said outcome of a respective treatment.

41. The method of claim 40, wherein said medical recommendation is a medical recommendation of a phase in an ongoing treatment and said outcome is a current outcome of said phase, said updating and repeating are performed during said ongoing treatment.

42. The method of claim 34, wherein said medical recommendation comprises a request for an additional evolution, further comprising:
- e) updating at least one of said plurality of patient medical records with said additional evolution; and
- f) repeating a)-d) wherein said current patient profile being updated with said additional evolution.

43. A method of medical imaging comprising:
- providing a reference database of medical pathological images of a plurality of patients, and information about a plurality of first biological activity indications associated with said respective reference images
- receiving a preliminary nuclear medical image derived from a current patient with information about at least one of a plurality of associated second biological activity indications;
  - identifying a match between one or more images in the reference database and the preliminary nuclear medical image using a computing device by comparing said plurality of second biological activity indications and one or more of said first biological activity indications; and using said matched images for further image data acquisition from said current patient,
- wherein said comparing is performed between predefined ranges which are set around values given at a multidimensional patient profile, and each one of the values and/or ranges is weighted according to importance, and wherein each said first and second plurality of biological activity indications comprises an uptake level of radiation emitted from a plurality of tracers.

44. An imaging system for capturing a medical image of at least one tissue of a patient, comprising:
- at least one radiation detector for obtaining a source nuclear medical image of a current patient associated with at least one first biological activity indication;
- a computer database configured for storing a plurality of reference medical pathology images derived from a plurality of patients, each image being stored with at least one associated second biological activity indication;
- image processing circuitry operative to analyze said source medical image, and to identify one or more reference medical images matching the source medical image according to said at least one first and second biological activity indications,
- wherein said analyzing is performed between predefined ranges which are set around values given at a multidimensional patient profile, and each one of the values and/or ranges is weighted according to importance; and
- an output circuit operable to instruct image data acquisition performed by said at least one detector according to said matching set, wherein each said first and second plurality of biological activity indications comprises an uptake level of radiation emitted from a plurality of tracers.

45. A method for obtaining a medical image of at least one tissue of a current patient, comprising:
- receiving a preliminary nuclear medical image of a current patient associated with at least one first biological activity indication;
- identifying a match between said at least one first biological activity and one or more biological activities respectively associated with a plurality of reference pathological medical images, said reference images comprising images of a plurality of patients;
- wherein said identifying is performed by matching predefined ranges which are set around values given at a multidimensional patient profile, each one of the values and/or ranges is weighted according to importance, and each said first and second plurality of biological activity indications comprises an uptake level of radiation emitted from a plurality of tracers and
- outputting instructions for obtaining an additional medical image of said current patient according to said matching.

* * * * *